US008871451B2

(12) United States Patent
Klee et al.

(10) Patent No.: US 8,871,451 B2
(45) Date of Patent: Oct. 28, 2014

(54) EXTRACELLULAR AND MEMBRANE-ASSOCIATED PROSTATE CANCER MARKERS

(75) Inventors: George G. Klee, Rochester, MN (US); George Vasmatzis, Byron, MN (US); Farhad Kosari, Rochester, MN (US); Eric W. Klee, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 183 days.

(21) Appl. No.: 13/607,296

(22) Filed: Sep. 7, 2012

(65) Prior Publication Data

US 2013/0004974 A1    Jan. 3, 2013

Related U.S. Application Data

(63) Continuation of application No. 12/442,685, filed as application No. PCT/US2007/079423 on Sep. 25, 2007, now Pat. No. 8,273,539.

(60) Provisional application No. 60/847,057, filed on Sep. 25, 2006.

(51) Int. Cl.
 *G01N 33/53* (2006.01)
 *C12Q 1/68* (2006.01)
 *G01N 33/574* (2006.01)

(52) U.S. Cl.
 CPC .... *G01N 33/57434* (2013.01); *C12Q 2600/158* (2013.01); *C12Q 1/6886* (2013.01); *G01N 33/57488* (2013.01); *G01N 33/57492* (2013.01); *C12Q 2600/106* (2013.01)
 USPC ......................................................... 435/7.1

(58) Field of Classification Search
 None
 See application file for complete search history.

(56) References Cited

U.S. PATENT DOCUMENTS

| | | |
|---|---|---|
| 5,143,854 A | 9/1992 | Pirrung et al. |
| 5,744,305 A | 4/1998 | Fodor et al. |
| 6,218,523 B1 | 4/2001 | French |
| 6,630,358 B1 | 10/2003 | Wagner et al. |
| 8,273,539 B2 | 9/2012 | Klee et al. |
| 8,338,109 B2 | 12/2012 | Vasmatzis et al. |
| 2002/0119463 A1 | 8/2002 | Faris |
| 2002/0182586 A1 | 12/2002 | Morris et al. |
| 2003/0119168 A1 | 6/2003 | Madison et al. |
| 2005/0202442 A1 | 9/2005 | Morris et al. |
| 2006/0211017 A1 | 9/2006 | Chinnaiyan et al. |
| 2007/0048738 A1 | 3/2007 | Donkena et al. |
| 2007/0212702 A1 | 9/2007 | Tomlins et al. |
| 2007/0275915 A1 | 11/2007 | Hallenbeck et al. |
| 2009/0036415 A1 | 2/2009 | Rubin et al. |
| 2009/0075921 A1 * | 3/2009 | Ikegawa et al. ................. 514/44 |
| 2009/0149333 A1 | 6/2009 | Knudsen et al. |
| 2009/0239221 A1 | 9/2009 | Chinnaiyan et al. |
| 2009/0298108 A1 | 12/2009 | Klee et al. |
| 2010/0130377 A1 | 5/2010 | Vasmatzis et al. |
| 2010/0257617 A1 | 10/2010 | Arul et al. |
| 2013/0085080 A1 | 4/2013 | Vasmatzis et al. |
| 2013/0302808 A1 | 11/2013 | Vasmatzis |

FOREIGN PATENT DOCUMENTS

| | | |
|---|---|---|
| WO | WO 02/00929 | 1/2002 |
| WO | WO 03/012067 | 2/2003 |
| WO | WO 2006/135596 | 12/2006 |
| WO | WO 2007/056049 | 5/2007 |
| WO | WO 2007/070621 | 6/2007 |
| WO | WO 2008/023087 | 2/2008 |
| WO | WO 2009/009432 | 1/2009 |
| WO | WO2009/020521 | 2/2009 |
| WO | WO 2009/045115 | 4/2009 |

OTHER PUBLICATIONS

Klee et al (Clinical Chemistry, 2012, 58(3): 599-609).*
U.S. Appl. No. 61/057,698, filed May 20, 2008, Klee et al.
Alberts et al., *Molecular Biology of the Cell*, 3$^{rd}$ Ed., 1994, p. 465.
Amling et al., "Long-term hazard of progression after radical prostatectomy for clinically localized prostate cancer continued risk of biochemical failure after 5 years," *J Urol.*, 2000, 164:101-105.
Amundadottir et al., "A common variant associated with prostate cancer in European and African populations," *Nat Genet.*, 2006, 38:652-658.
Amundson et al., "Integrating global gene expression and radiation survival parameters across the 60 cell lines of the National Cancer Institute Anticancer Drug Screen," *Cancer Research*, 2008, 68(2):415-424.
Ballman et al., "Faster cyclic loess: normalizing RNA arrays via linear models," *Bioinformatics*, 2004, 20:2778-2786.
Bergstralh et al., "Software for optimal matching in observational studies," *Epidemiology*, 1996, 7(3):331-332.
Best et al., "Molecular differentiation of high- and moderate-grade human prostate cancer by cDNA microarray analysis," *Diagn Mol Pathol.*, Jun. 2003, 12(2):63-70.
Bibikova et al., "Expression signatures that correlated with Gleason score and relapse in prostate cancer," *Genomics*, 2007, 89(6):666-672.
Bibikova et al., "Gene expression profiles in formalin-fixed, paraffin-embedded tissues obtained with a novel assay for microarray analysis," *Clin Chem.*, 2004, 50:2384-2386.
Bibikova et al., "Quantitative gene expression profiling in formalin-fixed, paraffin-embedded tissues using universal bead arrays," *Am J Pathol.*, 2004, 165:1799-1807.
Blute et al., "Use of Gleason score, prostate specific antigen, seminal vesicle and margin status to predict biochemical failure after radical prostatectomy," *J Urol*, 2001, 165:119-125.

(Continued)

*Primary Examiner* — Sean Aeder
(74) *Attorney, Agent, or Firm* — Fish & Richardson P.C.

(57) ABSTRACT

This document relates to methods and materials involved in identifying, assessing, and monitoring prostate cancer in male mammals. For example, this document provides arrays for detecting polypeptides or nucleic acids that can be used to identify prostate cancer in male mammals. In addition, methods and materials for assessing and monitoring prostate cancer in mammals are provided herein.

5 Claims, No Drawings

(56) References Cited

OTHER PUBLICATIONS

Bostwick et al., "Prognostic factors in prostate cancer: College of American Pathologists consensus statement," *Arch Pathol Lab Med*, 2000, 124(7):995-1000.
Breiman, "Random Forests," *Machine Learning*, 2001, 45:5-32.
Bull et al., "Identification of potential diagnostic markers of prostate cancer and prostatic intraepithelial neoplasia using cDNA microarray," *Br J Cancer*, Jun. 1, 2001, 84(11):1512-1519.
Chen et al., "Hepsin and maspin are inversely expressed in laser capture microdissectioned prostate cancer," *J Urol.*, Apr. 2003, 169(4):1316-1319.
Cheville et al., "Gene panel model predictive of outcome in men at high-risk of system progression and death from prostate cancer after radical retropubic prostatectomy," *J. Clin Oncol.*, Aug. 20, 2008, 26(24):3930-3936.
Cologne and Shibata, "Optimal Case-Control Matching in Practice Epidemiology," 6(3):271-275, May 1995.
D'Amico et al., "Cancer-specific mortality after surgery or radiation for patients with clinically localized prostate cancer managed during the prostate-specific antigen era," *J Clin Oncol.*, 2003, 21:2163-2172.
D'Amico et al., "Determinants of prostate cancer-specific survival after radiation therapy for patients with clinically localized prostate cancer," *J Clin Oncol.*, 2002, 20:4567-4573.
De Marzo et al., "Pathological and molecular mechanisms of prostate carcinogenesis: implications for diagnosis, detection, prevention, and treatment," *J Cell Biochem.*, Feb. 15, 2004, 91(3):459-477.
Demichelis et al., "TMPRSS2:ERG gene fusion associated with lethal prostate cancer in a watchful waiting cohort," *Oncogene*, 2007, 26(31):4596-4599.
Dhanasekaran et al., "Delineation of prognostic biomarkers in prostate cancer," *Nature*, 2001, 412:822-826.
Eder et al., "Genes differentially expressed in prostate cancer," *BJU Int.*, May 2004, 93(8):1151-1155.
Epstein et al., "Prognostic factors and reporting of prostate carcinoma in radical prostatectomy and pelvic lymphadenectomy specimens," *Scand. J. Urol. Nephrol. Suppl.*, 2005, 216:34-63.
Ernst et al., "Decrease and gain of gene expression are equally discriminatory markers for prostate carcinoma: a gene expression analysis on total and microdissected prostate tissue," *Am J Pathol.*, Jun. 2002, 160(6):2169-2180.
Fan et al., "Concordance among gene expression-based predictors for breast cancer," *N Engl J Med.*, 2006, 355:560-569.
Foley et al., "Molecular pathology of prostate cancer: the key to identifying new biomarkers of disease," *Endocrine-Related Cancer*, 2004, 11:477-488.
GenBank Accession No. AA462934 dated Jun. 10, 1997.
GenBank Accession No. AA920095 dated Apr. 20, 1998.
GenBank Accession No. AB028840 dated Jan. 12, 2000.
GenBank Accession No. AB030836 dated Oct. 23, 1999.
GenBank Accession No. AB036741 dated Dec. 22, 2000.
GenBank Accession No. AF077349 dated Dec. 14, 2000.
GenBank Accession No. AF077351 dated Dec. 20, 2000.
GenBank Accession No. AF115517 dated Nov. 23, 2005.
GenBank Accession No. AI413910 dated Feb. 9, 1999.
GenBank Accession No. AI414999 dated Feb. 9, 1999.
GenBank Accession No. AI425960 dated Mar. 9, 1999.
GenBank Accession No. AI851940 dated Jul. 15, 1999.
GenBank Accession No. AK018022 dated Sep. 19, 2008.
GenBank Accession No. AK019341 dated Sep. 19, 2008.
GenBank Accession No. AK019342 dated Sep. 19, 2008.
GenBank Accession No. AK034387 dated Sep. 19, 2008.
GenBank Accession No. AK038229 dated Sep. 19, 2008.
GenBank Accession No. AK038434 dated Sep. 19, 2008.
GenBank Accession No. AK041534 dated Sep. 19, 2008.
GenBank Accession No. AK042683 dated Sep. 19, 2008.
GenBank Accession No. AK136096 dated Sep. 19, 2008.
GenBank Accession No. AK136101 dated Sep. 19, 2008.
GenBank Accession No. AK142768 dated Sep. 19, 2008.
GenBank Accession No. AL591433 dated Jan. 15, 2009.
GenBank Accession No. BC004702 dated Jul. 15, 2006.
GenBank Accession No. BC055737 dated Jul. 15, 2006.
GenBank Accession No. BC086799 dated Sep. 21, 2006.
GenBank Accession No. BF449664 dated Dec. 1, 2000.
GenBank Accession No. BG063957 dated Jan. 26, 2001.
GenBank Accession No. BG077309 dated Dec. 17, 2003.
GenBank Accession No. BM114282 dated Jan. 30, 2002.
GenBank Accession No. BY023910 dated Dec. 6, 2002.
GenBank Accession No. CN724527 dated May 18, 2004.
GenBank Accession No. NM_000130 dated Oct. 18, 2009.
GenBank Accession No. NM_000493 dated Mar. 15, 2009.
GenBank Accession No. NM_000598, GI No. 62243067, dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001034 dated Oct. 5, 2009.
GenBank Accession No. NM_001039573, GI No. 221316683, dated Mar. 4, 2010, 5 pages.
GenBank Accession No. NM_001049 dated Jun. 21, 2009.
GenBank Accession No. NM_001067 dated Oct. 18, 2009.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_001786 dated Nov. 1, 2009.
GenBank Accession No. NM_001844 dated Sep. 28, 2009.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 7, 2010, 7 pages.
GenBank Accession No. NM_003873.3 dated Oct. 18, 2009.
GenBank Accession No. NM_004336; GI No. 211938448, dated Mar. 14, 2010, 6 pages.
GenBank Accession No. NM_004449 dated Jan. 8, 2012, 6 pages.
GenBank Accession No. NM_005025.2 dated Jul. 12, 2009.
GenBank Accession No. NM_005192, GI No. 195927023, dated Mar. 4, 2010, 4 pages.
GenBank Accession No. NM_005651.1 dated Oct. 27, 2009.
GenBank Accession No. NM_006265, GI No. 208879448, dated Apr. 11, 2010, 6 pages.
GenBank Accession No. NM_006558 dated Aug. 2, 2009.
GenBank Accession No. NM_006727 dated Oct. 18, 2009.
GenBank Accession No. NM_006819; GI No. 110225356, dated May 7, 2010, 5 pages.
GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_018930 dated Feb. 10, 2008.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated May 7, 2010, 5 pages.

(56) References Cited

OTHER PUBLICATIONS

GenBank Accession No. NM_052988, GI No. 237858573, dated May 7, 2010, 5 pages.
GenBank Accession No. NM_080546; GI No. 112363101, dated May 7, 2010, 6 pages.
GenBank Accession No. NM_080607 dated Sep. 3, 2009.
GenBank Accession No. NM_133445 dated Sep. 20, 2009.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.
GenBank Accession No. W34764 dated May 13, 1996.
Gleason, "Histologic grading and clinical staging of prostatic carcinoma," *Urologic pathology: the prostate*, (Tannenbaum, ed., 1977) Lea & Febiger, Philadelphia, PA, pp. 171-197.
Gleason, "Histologic grading of prostate cancer: a perspective," *Hum. Pathol.*, 1992,23(3):273-279.
Gleave et al., "Randomized comparative study of 3 versus 8-month neoadjuvant hormonal therapy before radical prostatectomy: biochemical and pathological effects," *J Urol.*, 2001,166:500-507.
Glinsky et al., "Gene expression profiling predicts clinical outcome of prostate cancer," *J Clin Invest.*, 2004, 113:913-923.
Glinsky et al., "Microarray analysis identifies a death-from-cancer signature predicting therapy failure in patients with multiple types of cancer," *J Clin Invest.*, 2005, 115:1503-1521.
Gonzalgo and Isaacs, "Molecular pathways to prostate cancer," *J Urol.*, Dec. 2003, 170(6 Pt 1):2444-2452.
Greenbaum et al., "Comparing protein abundance and mRNA expression levels on a genomic scale," *Genome Biology*, 2003, 4(9):117.1-117.8.
Haiman et al., "Multiple regions within 8q24 independently affect risk for prostate cancer," *Nat Genet.*, 2007, 39:638-644.
Harrell and Newson, Stata Journal, 6:309-334, 2006.
Henrotin et al., "Type II collagen peptides for measuring cartilage degradation," *Biotheology*, 2004, 41(3-4):Abstract.
Holzbeierlein et al., "Gene expression analysis of human prostate carcinoma during hormonal therapy identifies androgen-responsive genes and mechanisms of therapy resistance," *Am. J. Pathol.*, Jan. 2004, 164(1):217-227.
Hughes et al., "Molecular pathology of prostate cancer," *J Clin Pathol.*, Jul. 2005,58(7):673-684.
Humphrey et al., "Histologic grade, DNA ploidy, and intraglandular tumor extent as indicators of tumor progression of clinical Stage B prostatic carcinoma," *Am J Surg Pathol*, 1991, 15(12):1165-1170.
Jemal et al., "Cancer statistics," *CA Cancer J Clin.*, 2005, 55:10-30.
Karan et al., "Current status of the molecular genetics of human prostatic adenocarcinomas," *Int J Cancer*, Jan. 20, 2003 103(3):285-293.
Karayi and Markham, "Molecular biology of prostate cancer," *Prostate Cancer Prostatic Dis.*, 2004, 7(1):6-20
Kestin, "Potential survival advantage with early androgen deprivation for biochemical failure after external beam radiotherapy: the importance of accurately defining biochemical disease status," *Int J Rad Oncol Biol Phys.*, 2004, 60:453-62.
Klee et al., "Candidate serum biomarkers for prostate adenocarcinoma identified by mRNA differences in prostate tissue and verified with protein measurements in tissue and blood," *Clin Chem.*, 58(3):599-609, print Mar. 2012, Epub Jan. 2012.
Kosari et al., "Identification of biomarkers for prostate cancer," *Clin. Cancer Res.*, 2008, 1734-1743.
Kube et al., "Optimization of laser capture microdissection and RNA amplification for gene expression profiling of prostate cancer," *BMC Mol. Biol.*, 2007, 8:25.
Lapointe et al., "Gene expression profiling identifies clinically relevant subtypes of prostate cancer," *Proc Natl Acad Sci USA*, 2004, 101:811-816.
Latulippe et al., "Comprehensive Gene Expression Analysis of Prostate Cancer Reveals Distinct Transcriptional Programs Associated with Metastatic Disease," *Cancer Res.*, 2002, 62:4499-4506.
Lawton et al., "Updated results of the phase III Radiation Therapy Oncology Group (RTOG) trial 85-31 evaluating the potential benefit of androgen suppression following standard radiation therapy for unfavorable prognosis carcinoma of the prostate," *Int J Rad Oncol Biol Phys.*, 2001, 49:937-946.
Luo et al., "Gene expression analysis of prostate cancers," *Mol Carcinog.*, Jan. 2002, 33(1):25-35.
Luo et al., "Human Prostate Cancer and Benign Prostatic Hyperplasia: Molecular Dissection by Gene Expression Profiling," *Cancer Res.*, 2001, 61:4683-4688.
Magee et al., "Expression Profiling Reveals Hepsin Overexpression in Prostate Cancer," *Cancer Res.*, 2001, 61:5692-5696.
Montironi et al., "Carcinoma of the prostate: inherited susceptibility, somatic gene defects and androgen receptors," *Virchows Arch.*, Jun. 2004, 444(6):503-508.
Moul et al., "Early versus delayed hormonal therapy for prostate specific antigen only recurrence of prostate cancer after radical prostatectomy," *J Urol.*, 2004, 171:1141-1147.
Moul, "Prostate specific antigen only progression of prostate cancer," *J Urol.*, 2000, 163:1632-42.
Nakagawa et al., A Tissue Biomarker Panel Predicting Systemic Progression after PSA Recurrence Post-Definitive Prostate Cancer Therapy *PLos ONE*, 2008, 3(5):e2318, 14 pages.
Noordzij et al., "The prognostic value of CD44 isoforms in prostate cancer patients treated by radical prostatectomy," *Clin Cancer Res.*, 3(5):805-815, May 1997.
Ohl et al., "Gene expression studies in prostate cancer tissue: which reference gene should be selected for normalization?," *J. Mol. Med.*, 2005, 83:1014-1024.
Parker et al., "High expression levels of survivin protein independently predict a poor outcome for patients who undergo surgery for clear cell renal cell carcinoma," *Cancer*, 2006, 107:37-45.
Pascal et al., "Correlation of mRNA and protein levels: Cell type-specific gene expression of cluster designation antigens in the prostate," *BMC Genomics*, 2008, 9:246 (13 pages).
Patel et al., "Preoperative PSA velocity is an independent prognostic factor for relapse after radical prostatectomy," *J Clin Oncol.*, 2005, 23:6157-6162.
Pereira et al, "Coagulation factor V and VIII/V ratio as predictors of outcome in paracetamol induced fulminant hepatic failure: relation to other prognostic indicators," Gut, 1992, 33:98-102.
Pienta et al., "The current state of preclinical prostate cancer animal models," *The Prostate*, 2008, 68:629-639.
Pilepich et al., "Phase III radiation therapy oncology group (RTOG) trial 86-10 of androgen deprivation adjuvant to definitive radiotherapy in locally advanced carcinoma of the prostate," *Int J Rad Oncol Biol Phys.*, 2001, 50:1243-1252.
Pinover et al., "Validation of a treatment policy for patients with prostate specific antigen failure after three-dimensional conformal prostate radiation therapy," *Cancer*, 2003, 97:1127-1133.
Porkka and Visakorpi, "Molecular mechanisms of prostate cancer," *Eur Urol.*, Jun. 2004, 45(6):683-691.
Porkka et al., "RAD21 and KIAA0196 at 8q24 are amplified and overexpressed in prostate cancer," *Genes Chromosomes Cancer*, 2007, 39:1-10.
Pound et al., "Natural history of progression after PSA elevation following radical prostatectomy," *JAMA*, 1999, 281:1591-1597.
Rhodes et al., "Large-scale meta-analysis of cancer microarray data identifies common transcriptional profiles of neoplastic transformation and progression," *Proc Natl Acad Sci USA*, 2004, 101:9309-9314.
Rhodes et al., "ONCOMINE: A Cancer Microarray Database and Integrated Data-Mining Platform," *Neoplasia*, 2004, 6:1-6.
Robertson and Paulson, "DNA in radical prostatectomy specimens. Prognostic value of tumor ploidy,"*Acta Oncol*, 1991, 30(2):205-207.
Rubin and De Marzo, "Molecular genetics of human prostate cancer," *Mod Pathol.*, Mar. 2004, 17(3):380-388.
Sandler et al., "Overall survival after prostate-specific-antigen-detected recurrence following conformal radiation therapy," *Int J Rad Oncol Biol Phys.*, 2000, 48:629-633.

(56) References Cited

OTHER PUBLICATIONS

Saramaki et al., "Amplification of EIF3S3 gene is associated with advanced stage in prostate cancer," *Am J Pathol.*, 2001, 159:2089-2094.
Sato et al., "Clinical significance of alterations of chromosome 8 in high-grade, advanced, nonmetastatic prostate carcinoma," *J Natl Cancer Inst.*, 1999, 91:1574-1580.
Savinainen et al., "Expression and copy number analysis of TRPS 1, EIF3S3 and MYC genes in breast and prostate cancer," *Br J Cancer*, 2004, 90:1041-1046.
Savinainen et al., "Over expression of EIF3S3 promotes cancer cell growth," *Prostate*, 2006, 66:1144-1150.
Schumacher et al., "A Common 8q24 Variant in Prostate and Breast Cancer from a Large Nested Case-Control Study," *Cancer Res.*, 2007, 67:2951-2956.
Severi et al., "The common variant rs1447295 on chromosome 8q24 and prostate cancer risk: results from an Australian population based case-control study," *Cancer Epidemiol Biomarkers Prev.*, 2007, 16:610-611.
Shipley et al., "Radiation therapy for clinically localized prostate cancer: a multi-institutional pooled analysis," *JAMA*, 1999, 281:1598-1604.
Singh et al., "Gene expression correlates of clinical prostate cancer behavior," *Cancer Cell*, 2002, 1:203-209.
Stamey et al., "Molecular genetic profiling of Gleason grade 4/5 prostate cancers compared to benign prostatichyperplasia," *J Urol.*, Dec. 2001, 166(6):2171-2177.
Stephenson et al., "Integration of gene expression profiling and clinical variables to predict prostate carcinoma recurrence after radical prostatectomy," *Cancer*, Jul. 15, 2005, 104(2):290-298.
Subramanian et al., "Gene set enrichment analysis: A knowledge-based approach for interpreting genome-wide expression profiles," *Proc Natl Acad Sci USA*, 2005, 102:15545-15550.
Supplemental Table 3 of U.S. Appl. No. 61/057,698, filed May 30, 2008.
Supplemental Table 4 of U.S. Appl. No. 61/057,698, filed May 30, 2008.
Supplemental Table 5 of U.S. Appl. No. 61/057,698, filed May 30, 2008.
Supplemental Table 6 of U.S. Appl. No. 61/057,698, filed May 30, 2008.
Supplemental Tables 1 and 2 of U.S. Appl. No. 61/057,698, filed May 30, 2008.
Tockman et al., "Considerations in bringing a cancer biomarker to clinical application," *Cancer Research*, 1992, 52:2711s-2718s.
Tollefson et al., "Stratification of Patient Risk Based on Prostate-Specific Antigen Doubling Time After Radical Retropubic Prostatectomy," *Mayo Clin Proc.*, 2007, 82:422-427.
Tomlins et al., "Integrative molecular concept modeling of prostate cancer progression," *Nat Genet.*, 2007, 39:41-51.
Tomlins et al., "Recurrent Fusion of TMPRSS2 and ETS Transcription Factor Genes in Prostate Cancer," *Science*, 2005, 310(5748):644-648.
Tomlins et al., "TMPRSS2:ETV4 Gene Fusions Define a Third Molecular Subtype of Prostate Cancer," *Cancer Res.*, 2006, 66:3396-3400.
Tricoli et al., "Detection of prostate cancer and predicting progression: current and future diagnostic markers," *Clinical Cancer Research*, Jun. 15, 2004, 10:3943-3953.
Tsuchiya et al., "Clinical significance of alterations of chromosome 8 detected by fluorescence in situ hybridization analysis in pathologic organ-confined prostate cancer," *Genes Chromosomes Cancer*, 2002, 34:363-371.
Tsuchiya et al., "Mapping and gene expression profile of the minimally overrepresented 8q24 region in prostate cancer," *Am J Pathol.*, 2002, 160:1799-1806.
Varambally et al., "Integrative Genomic and Proteomic Analysis of Prostate Cancer Reveals Signatures of Metastatic Progression," *Cancer Cell*, Nov. 2005, 8(5):393-406.
Visakorpi, "The molecular genetics of prostate cancer," *Urology*, Dec. 29, 2003, 62 Suppl 1:19-35.
Wang et al., "Two common chromosome 8q24 variants are associated with increased risk for prostate cancer," *Cancer Res.*, 2007, 67:2944-2950.
Watson and Schalken, "Future opportunities for the diagnosis and treatment of prostate cancer," *Prostate Cancer Prostatic Dis.*, 2004, 7:S8-S13.
Welsh et al., "Analysis of Gene Expression Identifies Candidate Markers and Pharmacological Targets in Prostate Cancer," *Cancer Res.*, 2001, 61:5974-5978.
Winkler et al., "Stage D1 prostatic adenocarcinoma: significance of nuclear DNA ploidy patterns studied by flow cytometry," *Mayo Clin Proc*, 1988, 63(2):103-112.
Yeager et al., "Genome-wide association study of prostate cancer identifies a second risk locus at 8q24," *Nat Genet.*, 2007, 39:645-649.
Yu et al., "Gene expression alterations in prostate cancer predicting tumor aggression and preceding development of malignancy," *J Clin Oncol.*, Jul. 15, 2004, 22(14):2790-2799.
Zanetta et al., "Flow-cytometric analysis of deoxyribonucleic acid content in advanced ovarian carcinoma: its importance in long-term survival," *Am J Obstet Gynecol*, 1996, 175(5):1217-1225.
Zelefsky et al., "Neoadjuvant hormonal therapy improves the therapeutic ratio in patients with bulky prostatic cancer treated with three-dimensional conformal radiation therapy," *Int J Radiat Oncol Biol Phys.*, 1994, 29:755-761.
International Preliminary Report on Patentability for PCT/US2007/079423 mailed Apr. 9, 2009, 6 pages.
International Preliminary Report on Patentability for PCT/US2007/83504 mailed May 5, 2009, 4 pages.
International Preliminary Report on Patentability for PCT/US2011/043703, issued Jan. 22, 2013, 4 pages.
International Search Report and Written Opinion for PCT/US2011/043703, dated Mar. 27, 2012, 5 pages.
International Search Report/Written Opinion for PCT/US2007/079423 mailed Feb. 27, 2008, 10 pages.
International Search Report/Written Opinion for PCT/US2007/83504 mailed Apr. 14, 2008, 3 pages.
Office Action for U.S. Appl. No. 12/442,685, 12 pages, notification date May 24, 2011.
Office Action for U.S. Appl. No. 12/442,685, 8 pages, notification date Oct. 13, 2011.
Office Action for U.S. Appl. No. 12/474,879, 15 pages, notivicatin date Jan. 6, 2012.
Office Action in U.S. Appl. No. 12/474,879, dated Aug. 16, 2012, 17 pages.
Office Action in U.S. Appl. No. 12/513,329, dated May 29, 2012, 22 pages.
Office Action in U.S. Appl. No. 13/513,329, dated Jan. 30, 2012, 18 pages.
Chen et al., "Significance of noninvasive diagnosis of prostate cancer with cytologic examination of prostatic fluid," J Nippon Med Sch., 73(3):129-135, Jun. 2006.
Edwards et al., "Expression analysis onto microarrays of randomly selected cDNA clones highlights HOXB13 as a marker of human prostate cancer," Br J Cancer., 92(2):376-381, Jan. 31, 2005.
Hughes et al., "Topoisomerase II-α expression increases with increasing Gleason score and with hormone insensitivity in prostate carcinoma," J Clin Pathol., 59(7): 721-724, Jul. 2006.
Ida et al., "Topoisomerase II alpha protein expression Is predictive of outcome in Gleason score ≥ 7 prostate cancer patients treated surgically and is dependent on ERG status." Mod Pathol., Abstract 1895, 23: 424A-425A, Feb. 2010.
Karnes et al., "Radical prostatectomy for high-risk prostate cancer," Jpn. J. Clin. Oncol., 40 (1): 3-9, Epub Oct. 19, 2009.
Karnes et al., "The ability of biomarkers to predict systemic progression in men with high-risk prostate cancer treated surgically is dependent on ERG status," Cancer Res., 70(22):8994-9002, Epub Nov. 9, 2010.
Kumar-Sinha and Chinnaiyan, "Molecular markers to identify patients at risk for recurrence after primary treatment for prostate cancer," Urology, 62 Suppl 1:19-35, Dec. 29, 2003.

(56) References Cited

OTHER PUBLICATIONS

Visakorpi, "The molecular genetics of prostate cancer," Urology, 62(5 Suppl 1):3-10, Nov. 2003.

Willman and Holden, "Immunohistochemical staining for DNA topoisomerase II-alpha in benign, premalignant, and malignant lesions of the prostate," Prostate, 42(4):280-286, Mar. 1, 2000.

* cited by examiner

```
                    SEQUENCE LISTING

<160> NUMBER OF SEQ ID NOS: 63

<210> SEQ ID NO 1
<211> LENGTH: 13
<212> TYPE: PRT
<213> ORGANISM: Homo sapiens

<400> SEQUENCE: 1

Ser Tyr Asp Leu Asp Pro Gly Ala Gly Ser Leu Glu Ile
1               5                   10

<210> SEQ ID NO 2
<211> LENGTH: 10
<212> TYPE: PRT
<213> ORGANISM: Homo sapiens

<400> SEQUENCE: 2

Ile Gln Asp Ile Asn Asp Asn Glu Pro Lys
1               5                   10

<210> SEQ ID NO 3
<211> LENGTH: 18
<212> TYPE: PRT
<213> ORGANISM: Homo sapiens

<400> SEQUENCE: 3

Gly Glu Gln Gly Pro Pro Gly Ile Pro Gly Pro Gln Gly Leu Pro Gly
1               5                   10                  15

Val Lys

<210> SEQ ID NO 4
<211> LENGTH: 13
<212> TYPE: PRT
<213> ORGANISM: Homo sapiens

<400> SEQUENCE: 4

Glu Leu Gln Glu Thr Asn Ala Ala Leu Gln Asp Val Arg
1               5                   10
```

<210> SEQ ID NO 5
<211> LENGTH: 12
<212> TYPE: PRT
<213> ORGANISM: Homo sapiens

<400> SEQUENCE: 5

Leu Val Pro Asn Pro Gly Gln Glu Asp Ala Asp Arg
1               5                   10

<210> SEQ ID NO 6
<211> LENGTH: 13
<212> TYPE: PRT
<213> ORGANISM: Homo sapiens

<400> SEQUENCE: 6

Asn Gln Gly Thr Ser Asp Phe Leu Pro Ser Arg Pro Arg
1               5                   10

<210> SEQ ID NO 7
<211> LENGTH: 10
<212> TYPE: PRT
<213> ORGANISM: Homo sapiens

<400> SEQUENCE: 7

Glu Pro Pro Ala Ala Pro Gly Ala Trp Arg
1               5                   10

<210> SEQ ID NO 8
<211> LENGTH: 10
<212> TYPE: PRT
<213> ORGANISM: Homo sapiens

<400> SEQUENCE: 8

Val Ala Glu Asn Glu Asn Pro Gly Ala Arg
1               5                   10

<210> SEQ ID NO 9
<211> LENGTH: 18
<212> TYPE: PRT
<213> ORGANISM: Homo sapiens

<400> SEQUENCE: 9

Gly Ala Asn Gly Asp Pro Gly Arg Pro Gly Glu Pro Gly Leu Pro Gly
1               5                   10                  15

Ala Arg

<210> SEQ ID NO 10
<211> LENGTH: 16
<212> TYPE: PRT
<213> ORGANISM: Homo sapiens

<400> SEQUENCE: 10

Ala Gly Glu Pro Gly Leu Gln Gly Pro Ala Gly Pro Pro Gly Glu Lys
1               5                   10                  15

<210> SEQ ID NO 11
<211> LENGTH: 15
<212> TYPE: PRT
<213> ORGANISM: Homo sapiens

<400> SEQUENCE: 11

Gly Pro Pro Gly Pro Gln Gly Pro Ala Gly Glu Gln Gly Pro Arg
1               5                   10                  15

<210> SEQ ID NO 12
<211> LENGTH: 19
<212> TYPE: PRT
<213> ORGANISM: Homo sapiens

<400> SEQUENCE: 12

Ala Gly Pro Asp Gly Pro Asp Gly Lys Pro Gly Ile Asp Gly Leu Thr
1               5                   10                  15

Gly Ala Lys

<210> SEQ ID NO 13
<211> LENGTH: 15
<212> TYPE: PRT
<213> ORGANISM: Homo sapiens

<400> SEQUENCE: 13

Gly Ile Leu Gly Asp Pro Gly His Gln Gly Lys Pro Gly Pro Lys
1               5                   10                  15

<210> SEQ ID NO 14
<211> LENGTH: 17
<212> TYPE: PRT
<213> ORGANISM: Homo sapiens

<400> SEQUENCE: 14

Ala Thr Asp Pro Asp Glu Gly Ala Asn Gly Asp Val Thr Tyr Ser Phe
1               5                   10                  15

Arg

<210> SEQ ID NO 15
<211> LENGTH: 12
<212> TYPE: PRT
<213> ORGANISM: Homo sapiens

<400> SEQUENCE: 15

His Leu Thr Pro Val Thr Leu Glu Leu Gly Gly Lys
1               5                   10

<210> SEQ ID NO 16
<211> LENGTH: 14
<212> TYPE: PRT
<213> ORGANISM: Homo sapiens

<400> SEQUENCE: 16

Ser Gly Val Gln Gln Leu Ile Gln Tyr Tyr Gln Asp Gln Lys
1               5                   10

<210> SEQ ID NO 17
<211> LENGTH: 17
<212> TYPE: PRT
<213> ORGANISM: Homo sapiens

<400> SEQUENCE: 17

Leu Tyr Leu Ser His Asn Gln Leu Ser Glu Ile Pro Leu Asn Leu Pro
1               5                   10                  15

Lys

<210> SEQ ID NO 18
<211> LENGTH: 19
<212> TYPE: PRT
<213> ORGANISM: Homo sapiens -continued

```
<400> SEQUENCE: 18

Ala Leu Glu Ile Leu Gln Glu Glu Asp Leu Ile Asp Glu Asp Asp Ile
1               5                   10                  15

Pro Val Arg

<210> SEQ ID NO 19
<211> LENGTH: 19
<212> TYPE: PRT
<213> ORGANISM: Homo sapiens

<400> SEQUENCE: 19

Ala Leu Glu Ile Leu Gln Glu Glu Asp Leu Ile Asp Glu Asp Asp Ile
1               5                   10                  15

Pro Val Arg

<210> SEQ ID NO 20
<211> LENGTH: 17
<212> TYPE: PRT
<213> ORGANISM: Homo sapiens

<400> SEQUENCE: 20

Gly His Leu Phe Leu Gln Thr Asp Gln Pro Ile Tyr Asn Pro Gly Gln
1               5                   10                  15

Arg

<210> SEQ ID NO 21
<211> LENGTH: 13
<212> TYPE: PRT
<213> ORGANISM: Homo sapiens

<400> SEQUENCE: 21

Gly Leu Glu Glu Glu Leu Gln Phe Ser Leu Gly Ser Lys
1               5                   10

<210> SEQ ID NO 22
<211> LENGTH: 19
<212> TYPE: PRT
<213> ORGANISM: Homo sapiens

<400> SEQUENCE: 22

Asn Tyr Tyr Ile Ala Ala Glu Glu Ile Ser Trp Asp Tyr Ser Glu Phe
1               5                   10                  15

Val Gln Arg

<210> SEQ ID NO 23
<211> LENGTH: 14
<212> TYPE: PRT
<213> ORGANISM: Homo sapiens

<400> SEQUENCE: 23

Ser Tyr Thr Ile His Tyr Ser Glu Gln Gly Val Glu Trp Lys
1               5                   10

<210> SEQ ID NO 24
<211> LENGTH: 19
<212> TYPE: PRT
<213> ORGANISM: Homo sapiens

<400> SEQUENCE: 24

Asp Gly Leu Asp Ile Gln Leu Pro Gly Asp Asp Pro His Ile Ser Val
1               5                   10                  15
```

Gln Phe Arg

<210> SEQ ID NO 25
<211> LENGTH: 11
<212> TYPE: PRT
<213> ORGANISM: Homo sapiens

<400> SEQUENCE: 25

His His Val Leu His Asp Gln Glu Val Asp Arg
1               5                   10

<210> SEQ ID NO 26
<211> LENGTH: 17
<212> TYPE: PRT
<213> ORGANISM: Homo sapiens

<400> SEQUENCE: 26

Gln Tyr Leu Leu Leu Asp Ser His Thr Gly Asn Leu Leu Thr Asn Glu
1               5                   10                  15

Lys

<210> SEQ ID NO 27
<211> LENGTH: 12
<212> TYPE: PRT
<213> ORGANISM: Homo sapiens

<400> SEQUENCE: 27

Asp Ile Asn Asp His Ala Pro Val Phe Gln Asp Lys
1               5                   10

<210> SEQ ID NO 28
<211> LENGTH: 21
<212> TYPE: PRT
<213> ORGANISM: Homo sapiens

<400> SEQUENCE: 28

Ile Leu Glu Asp Gln Glu Glu Asn Pro Leu Pro Ala Ala Leu Val Gln
1               5                   10                  15

Pro His Thr Gly Lys
            20

<210> SEQ ID NO 29
<211> LENGTH: 24
<212> TYPE: PRT
<213> ORGANISM: Homo sapiens

<400> SEQUENCE: 29

Phe Asn Leu Asp Leu Thr His Pro Val Glu Asp Gly Ile Phe Asp Ser
1               5                   10                  15

Gly Asn Phe Glu Gln Phe Leu Arg
            20

<210> SEQ ID NO 30
<211> LENGTH: 9
<212> TYPE: PRT
<213> ORGANISM: Homo sapiens

<400> SEQUENCE: 30

Tyr Glu Ala Ala Val Pro Asp Pro Arg
1               5

<210> SEQ ID NO 31
<211> LENGTH: 11

```
<212> TYPE: PRT
<213> ORGANISM: Homo sapiens

<400> SEQUENCE: 31

Glu Thr Gly Leu Glu Thr Ser Ser Gly Gly Lys
1               5                   10

<210> SEQ ID NO 32
<211> LENGTH: 11
<212> TYPE: PRT
<213> ORGANISM: Homo sapiens

<400> SEQUENCE: 32

Asp Ile Ile Pro Glu Thr Leu Phe Ile Pro Arg
1               5                   10

<210> SEQ ID NO 33
<211> LENGTH: 11
<212> TYPE: PRT
<213> ORGANISM: Homo sapiens

<400> SEQUENCE: 33

Val Glu Ala Glu Asn Thr His Val Asp Pro Arg
1               5                   10

<210> SEQ ID NO 34
<211> LENGTH: 10
<212> TYPE: PRT
<213> ORGANISM: Homo sapiens

<400> SEQUENCE: 34

Ser Ser His Pro Glu Thr Tyr Gln Gln Arg
1               5                   10

<210> SEQ ID NO 35
<211> LENGTH: 9
<212> TYPE: PRT
<213> ORGANISM: Homo sapiens

<400> SEQUENCE: 35

Thr Val Glu Ser Leu Pro Asn Leu Arg
1               5

<210> SEQ ID NO 36
<211> LENGTH: 11
<212> TYPE: PRT
<213> ORGANISM: Homo sapiens

<400> SEQUENCE: 36

Ile Asp Asn Pro His Ile Thr Tyr Thr Ala Arg
1               5                   10

<210> SEQ ID NO 37
<211> LENGTH: 10
<212> TYPE: PRT
<213> ORGANISM: Homo sapiens

<400> SEQUENCE: 37

Gly Thr Thr Gly Thr Gln Leu Asn Gly Arg
1               5                   10

<210> SEQ ID NO 38
<211> LENGTH: 7
<212> TYPE: PRT
<213> ORGANISM: Homo sapiens
```

```
<400> SEQUENCE: 38

Trp Leu Gln Gln Glu Val Lys
 1               5

<210> SEQ ID NO 39
<211> LENGTH: 17
<212> TYPE: PRT
<213> ORGANISM: Homo sapiens

<400> SEQUENCE: 39

Ala Glu Gly Gln Trp Thr Leu Glu Ile Gln Asp Leu Pro Ser Gln Val
 1               5                  10                  15

Arg

<210> SEQ ID NO 40
<211> LENGTH: 13
<212> TYPE: PRT
<213> ORGANISM: Homo sapiens

<400> SEQUENCE: 40

Gly Leu Pro Trp Gln Ser Ser Asp Gln Asp Ile Ala Arg
 1               5                  10

<210> SEQ ID NO 41
<211> LENGTH: 17
<212> TYPE: PRT
<213> ORGANISM: Homo sapiens

<400> SEQUENCE: 41

Asp Lys Leu Arg Lys Glu Ser Lys Asn Leu Asn Ile Gln Gly Ser Lys
 1               5                  10                  15

Phe

<210> SEQ ID NO 42
<211> LENGTH: 11
<212> TYPE: PRT
<213> ORGANISM: Homo sapiens

<400> SEQUENCE: 42

Ile Glu Ala Leu Ser Ser Ala Leu Gln Ile Phe
 1               5                  10

<210> SEQ ID NO 43
<211> LENGTH: 16
<212> TYPE: PRT
<213> ORGANISM: Homo sapiens

<400> SEQUENCE: 43

Leu Gly Ser Pro Leu Arg Gly Gly Ser Ser Leu Arg His Val Val Tyr
 1               5                  10                  15

<210> SEQ ID NO 44
<211> LENGTH: 12
<212> TYPE: PRT
<213> ORGANISM: Homo sapiens

<400> SEQUENCE: 44

Leu Ser Glu Pro Ala Glu Leu Thr Asp Ala Val Lys
 1               5                  10

<210> SEQ ID NO 45
<211> LENGTH: 12
```

```
<212> TYPE: PRT
<213> ORGANISM: Homo sapiens

<400> SEQUENCE: 45

His Ser Gln Pro Trp Gln Val Leu Val Ala Ser Arg
1               5                   10

<210> SEQ ID NO 46
<211> LENGTH: 9
<212> TYPE: PRT
<213> ORGANISM: Homo sapiens

<400> SEQUENCE: 46

Glu Thr His Ala Ser Ala Pro Val Lys
1               5

<210> SEQ ID NO 47
<211> LENGTH: 13
<212> TYPE: PRT
<213> ORGANISM: Homo sapiens

<400> SEQUENCE: 47

Gly Leu Gly Ala Thr Thr His Pro Thr Ala Ala Val Lys
1               5                   10

<210> SEQ ID NO 48
<211> LENGTH: 13
<212> TYPE: PRT
<213> ORGANISM: Homo sapiens

<400> SEQUENCE: 48

Gln Leu Cys Ala Pro Pro Asp Gln Pro Trp Val Glu Arg
1               5                   10

<210> SEQ ID NO 49
<211> LENGTH: 16
<212> TYPE: PRT
<213> ORGANISM: Homo sapiens

<400> SEQUENCE: 49

Glu Ile Pro Ala Trp Val Pro Glu Asp Pro Ala Ala Gln Ile Thr Lys
1               5                   10                  15

<210> SEQ ID NO 50
<211> LENGTH: 10
<212> TYPE: PRT
<213> ORGANISM: Homo sapiens

<400> SEQUENCE: 50

Thr Pro Asp Val Ser Ser Ala Leu Asp Lys
1               5                   10

<210> SEQ ID NO 51
<211> LENGTH: 14
<212> TYPE: PRT
<213> ORGANISM: Homo sapiens

<400> SEQUENCE: 51

Thr Thr Asn Ile Gln Gly Ile Asn Leu Leu Phe Ser Ser Arg
1               5                   10

<210> SEQ ID NO 52
<211> LENGTH: 16
<212> TYPE: PRT
<213> ORGANISM: Homo sapiens
```

<400> SEQUENCE: 52

Glu Ile Pro Ala Trp Val Pro Phe Asp Pro Ala Ala Gln Ile Thr Lys
1               5                   10                  15

<210> SEQ ID NO 53
<211> LENGTH: 16
<212> TYPE: PRT
<213> ORGANISM: Homo sapiens

<400> SEQUENCE: 53

Glu Leu Pro Ala Ala Val Ala Pro Ala Gly Pro Ala Ser Leu Ala Arg
1               5                   10                  15

<210> SEQ ID NO 54
<211> LENGTH: 21
<212> TYPE: PRT
<213> ORGANISM: Homo sapiens

<400> SEQUENCE: 54

Pro Leu Pro Glu Pro Leu Thr Val Gln Leu Leu Thr Val Pro Gly Glu
1               5                   10                  15

Val Phe Pro Pro Lys
            20

<210> SEQ ID NO 55
<211> LENGTH: 12
<212> TYPE: PRT
<213> ORGANISM: Homo sapiens

<400> SEQUENCE: 55

Val Ala Ile Gly Gly Gln Ser Asn Glu Ser Asp Arg
1               5                   10

<210> SEQ ID NO 56
<211> LENGTH: 11
<212> TYPE: PRT
<213> ORGANISM: Homo sapiens

<400> SEQUENCE: 56

Leu Leu Pro Ala Leu Gln Ser Thr Ile Thr Arg
1               5                   10

<210> SEQ ID NO 57
<211> LENGTH: 15
<212> TYPE: PRT
<213> ORGANISM: Homo sapiens

<400> SEQUENCE: 57

Gln Gly Gly Val Asn Ala Thr Gln Val Leu Ile Gln His Leu Arg
1               5                   10                  15

<210> SEQ ID NO 58
<211> LENGTH: 13
<212> TYPE: PRT
<213> ORGANISM: Homo sapiens

<400> SEQUENCE: 58

Leu Glu Gly His Gly Asp Pro Leu His Glu Glu Val Lys
1               5                   10

<210> SEQ ID NO 59
<211> LENGTH: 12
<212> TYPE: PRT

```
<213> ORGANISM: Homo sapiens

<400> SEQUENCE: 59

Asp Leu Gly Leu Ala Glu Gly Glu Leu Ala Ala Arg
 1               5                  10

<210> SEQ ID NO 60
<211> LENGTH: 14
<212> TYPE: PRT
<213> ORGANISM: Homo sapiens

<400> SEQUENCE: 60

Ser Ile Leu Gln Gly Gln Pro Tyr Phe Ser Val Glu Pro Lys
 1               5                  10

<210> SEQ ID NO 61
<211> LENGTH: 14
<212> TYPE: PRT
<213> ORGANISM: Homo sapiens

<400> SEQUENCE: 61

Phe Leu Ser Leu Gly Pro Phe Ser Asp Thr Thr Val Lys
 1               5                  10

<210> SEQ ID NO 62
<211> LENGTH: 22
<212> TYPE: PRT
<213> ORGANISM: Homo sapiens

<400> SEQUENCE: 62

Ile Ala Val Ile Gly His Ser Phe Gly Gly Ala Thr Val Ile Gln Thr
 1               5                  10                  15

Leu Ser Glu Asp Gln Arg
                20

<210> SEQ ID NO 63
<211> LENGTH: 10
<212> TYPE: PRT
<213> ORGANISM: Homo sapiens

<400> SEQUENCE: 63

Val Gly Asp Thr Leu Asn Leu Asn Leu Arg
 1               5                  10
```

EXTRACELLULAR AND MEMBRANE-ASSOCIATED PROSTATE CANCER MARKERS

RELATED APPLICATIONS

This application is a continuation of U.S. patent application Ser. No. 12/442,685, filed on Mar. 24, 2009, which is a National Stage application under 35 U.S.C. §371 of International Application No. PCT/US2007/079423, having an International Filing Date of Sep. 25, 2007, which claims the benefit of priority to U.S. Provisional Patent Application Ser. No. 60/847,057, filed on Sep. 25, 2006. The disclosures of these applications are incorporated herein by reference in their entirety.

BACKGROUND

1. Technical Field

This document relates to methods and materials involved in identifying, assessing, and monitoring prostate cancer in male mammals.

2. Background Information

Cancer is a general term for diseases characterized by uncontrolled, abnormal growth of cells. The resulting mass, or tumor, can invade and destroy surrounding normal tissues. In addition, cancer cells from the tumor can spread through the blood or lymph to start new cancers in other parts of the body, or metastases.

Prostate cancer occurs when a malignant tumor forms in the tissue of the prostate. The prostate is a gland in the male reproductive system located below the bladder and in front of the rectum. The main function of the prostate gland, which is about the size of a walnut, is to make fluid for semen. Although there are several cell types in the prostate, nearly all prostate cancers start in the gland cells. This type of cancer is known as adenocarcinoma.

Prostate cancer is the second leading cause of cancer-related death in American men. Most of the time, prostate cancer grows slowly. Autopsy studies show that many older men who died of other diseases also had prostate cancer that neither they nor their doctor were aware of. Sometimes, however, prostate cancer can grow and spread quickly. It is important to be able to distinguish prostate cancers that will grow slowly from those that will grow quickly since treatment can be especially effective when the cancer has not spread beyond the region of the prostate. Finding ways to detect cancers early can improve survival rates.

SUMMARY

This document provides methods and materials related to identifying, assessing, and monitoring prostate cancer in male mammals (e.g., humans). For example, this document provides arrays for detecting polypeptides or nucleic acids that can be used to identify prostate cancer in mammals. Such arrays can allow prostate cancer to be identified in mammals based on differences in the levels of many polypeptides or nucleic acids in biological samples from mammals that have prostate cancer as compared to the corresponding levels in biological samples from mammals that do not have prostate cancer.

Screening for prostate cancer has been widely performed by measuring serum levels of prostate-specific antigen (PSA). However, effective use of the PSA serum assay in general population screening is inhibited by a lack of sensitivity and specificity. Specific, sensitive, and non-invasive methods of screening mammals for cancer (e.g., prostate cancer) can allow cancer to be detected earlier. Early detection of cancer in mammals can allow the mammals to be treated sooner and improve their prognosis. Screening methods having adequate specificity with low false positive rates can reduce unnecessary treatment and suffering.

This document is based, in part, on the discovery of nucleic acid sequences that are predicted to encode extracellular or membrane-associated polypeptides, and that are differentially expressed in cancerous and non-cancerous prostate epithelial cells. This document also is based, in part, on the discovery of nucleic acid sequences that are predicted to encode polypeptides, and that are expressed in prostate cells at a high level relative to other cell types. The levels of transcripts and/or polypeptides encoded by these nucleic acids can be used to distinguish mammals with prostate cancer from mammals without prostate cancer. For example, a mammal that is found to have serum containing one or more than one polypeptide encoded by a nucleic acid listed in Table 2 at a level that is different (e.g., greater than or less than) than the average level observed in control serum can be classified as having prostate cancer. In some cases, a mammal that is found to have serum containing one or more than one polypeptide encoded by a nucleic acid listed in Table 2 and one or more than one polypeptide encoded by a nucleic acid listed in Table 3 at a level that is different (e.g., greater than or less than) than the average level observed in control serum can be classified as having prostate cancer. In some cases, a mammal that is found to have prostate cells expressing one or more than one polypeptide encoded by a nucleic acid listed in Table 4 at a level that is greater than the average level observed in control prostate cells can be classified as having prostate cancer. The levels of nucleic acids and/or polypeptides encoded by nucleic acids listed in Table 2 also can be used to evaluate cancer aggressiveness, monitor cancer progression, predict cancer outcome, and monitor response to treatment in mammals. In some cases, the level of one or more than one nucleic acid or polypeptide encoded by a nucleic acid listed in Table 2 and the level of one or more than one nucleic acid or polypeptide encoded by a nucleic acid listed in Table 3 can be used to evaluate cancer aggressiveness, monitor cancer progression, predict cancer outcome, or monitor the response to cancer treatment in mammals.

In general, one aspect of this document features a method for identifying a mammal as having prostate cancer. The method comprising, or consists essentially of, (a) determining whether or not a mammal has a prostate cancer fluid profile, and (b) classifying the mammal as having prostate cancer if the mammal has the prostate cancer fluid profile and classifying the mammal as not having prostate cancer if the mammal does not have the prostate cancer fluid profile. The mammal can be a human. The method can comprise using blood, serum, plasma, urine, semen, or seminal fluid to assess the presence or absence of the prostate cancer fluid profile.

In another aspect, this document features a method for identifying a mammal as having prostate cancer. The method comprises, or consists essentially of, (a) determining whether or not a mammal has a prostate cancer cell profile, and (b) classifying the mammal as having prostate cancer if the mammal has the prostate cancer cell profile and classifying the mammal as not having prostate cancer if the mammal does not have the prostate cancer cell profile. The mammal can be a human. The method can comprise using prostate cells obtained from a needle biopsy to assess the presence or absence of the prostate cancer cell profile.

In another aspect, this document features a method for assessing the effectiveness of a treatment for prostate cancer.

The method comprises, of consists essentially of, determining whether or not a mammal having prostate cancer and having received a treatment for the prostate cancer has a prostate cancer fluid profile to the same or greater degree than that observed prior to the treatment, wherein the presence of the prostate cancer fluid profile to the same or greater degree than that observed prior to the treatment indicates that the treatment is ineffective. The mammal can be a human. The method can comprise using blood, serum, plasma, urine, semen, or seminal fluid to assess the presence or absence of the prostate cancer fluid profile to the same or greater degree than that observed prior to the treatment.

In another aspect, this document features a method for assessing the effectiveness of a treatment for prostate cancer. The method comprises, or consists essentially of, determining whether or not a mammal having prostate cancer and having received a treatment for the prostate cancer has a prostate cancer cell profile to the same or greater degree than that observed prior to the treatment, wherein the presence of the prostate cancer cell profile to the same or greater degree than that observed prior to the treatment indicates that the treatment is ineffective. The mammal can be a human. The method can comprise using prostate cells obtained from a needle biopsy to assess the presence or absence of the prostate cancer cell profile to the same or greater degree than that observed prior to the treatment.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references (e.g., the records associated with GenBank accession or GI numbers) mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods and materials related to identifying, assessing, and monitoring prostate cancer in male mammals. For example, this document provides arrays for detecting nucleic acids or polypeptides that can be used to identify, assess, and/or monitor prostate cancer in male mammals. Such arrays can allow prostate cancer to be identified, assessed, and/or monitored based on the levels of nucleic acids or polypeptides in a biological sample from a mammal.

As described herein, this document provides methods and materials for identifying prostate cancer in male mammals (e.g., humans). In some embodiments, a mammal can be classified as having prostate cancer if it is determined that a biological fluid (e.g., blood, urine, seminal fluid, or serum) from the mammal contains one or more than one polypeptide (e.g., two, three, four, five, six, seven, eight, nine, 10, 15, 20, 25, 30, 35, 40, 45, 50, 55, 60, or more than 60 polypeptides), or a fragment thereof, encoded by a nucleic acid listed in Table 2 (e.g., a category 1, 2, or 3 nucleic acid listed in Table 2) at a level that is greater than the average level of the same one or more than one polypeptide observed in corresponding control fluid from control mammals. In some cases, a mammal can be classified as having prostate cancer if it is determined that a biological fluid (e.g., blood, urine, seminal fluid, or serum) from the mammal contains one or more than one polypeptide, or fragment thereof, encoded by a nucleic acid listed in Table 2, and one or more than one polypeptide, or fragment thereof, encoded by a nucleic acid listed in Table 3 at a level that is greater than the average level of the same one or more than one polypeptide observed in corresponding control fluid from control mammals. In some cases, a mammal can be classified as having prostate cancer if it is determined that prostate cells from the mammal contain one or more than one nucleic acid or polypeptide, or fragment thereof, encoded by a nucleic acid listed in Table 4 (e.g., a category 1, 2, or 3 nucleic acid listed in Table 4) at a level that is greater than the average level (e.g., via a subset analysis) of the same one or more than one nucleic acid or polypeptide in corresponding control (e.g., non-cancerous) prostate cells.

In some cases, a mammal can be classified as having prostate cancer if it is determined that a biological fluid (e.g., blood, urine, seminal fluid, or semen) from the mammal has a prostate cancer fluid profile. For the purpose of this document, the term "prostate cancer fluid profile" as used herein refers to a polypeptide profile in a biological fluid (e.g., blood, plasma, serum, urine, semen, or seminal fluid) where 16 or more (e.g., 18, 20, 25, 30, 35, 40, 45, 50, 55, 60, or more) polypeptides, or fragments thereof, encoded by nucleic acids listed in Table 2 are present at a level greater than the level observed in a corresponding control biological fluid from a control mammal. In some cases, the prostate cancer fluid profile can be a polypeptide profile in a biological fluid where 25, 30, 35, 40, 45, 50, 55, 60, 65, 70, 75, 80, 85, 90, 95, or 100 percent of the polypeptides, or fragments thereof, encoded by nucleic acids listed in Table 2 are present at a level greater than the level observed in corresponding control biological fluid from a control mammal.

In some cases, a mammal can be classified as having prostate cancer if it is determined that prostate cells from the mammal have a prostate cancer cell profile. The term "prostate cancer cell profile" as used herein refers to a profile where prostate cells express 12 or more (e.g., 15, 20, 25, 30, 35, 40, 45, 50, 55, 60, or more) nucleic acids or polypeptides, or fragments thereof, encoded by nucleic acids listed in Table 4 at a level greater than the level observed in corresponding control prostate cells. In some cases, the prostate cancer cell profile can be a profile in prostate cells where 25, 30, 35, 40, 45, 50, 55, 60, 65, 70, 75, 80, 85, 90, 95, or 100 percent of the nucleic acids or polypeptides, or fragments thereof, encoded by nucleic acids listed in Table 4 are present at a level greater than the level observed in corresponding control prostate cells.

Prostate cancer can be identified in any male mammal such as a male human, dog, horse, mouse, or rat. The mammal can be middle-aged or older. For example, a male human can be 35 years old or older (e.g., 40, 45, 50, 55, 60, 65, 70, 75 years old or older).

Any biological fluid can be evaluated to determine if it contains one or more than one polypeptide or nucleic acid, or fragment thereof, encoded by a nucleic acid listed in Table 2 at a level that is greater than the average level observed in a corresponding control biological fluid. For example, blood (e.g., peripheral blood or venous prostate blood), plasma, serum, urine, semen, and/or seminal fluid can be evaluated to determine if the fluid contains one or more than one polypeptide or nucleic acid encoded by a nucleic acid listed in Table 2 at a level that is greater than the average level observed in a corresponding control biological fluid. In some cases, a biological fluid (e.g., blood, plasma, serum, urine, semen, and/or seminal fluid) can be evaluated to determine if the fluid contains one or more than one polypeptide or nucleic acid, or fragment thereof, encoded by a nucleic acid listed in Table 2, and one or more than one polypeptide or nucleic acid, or fragment thereof, encoded by a nucleic acid listed in Table 3 at a level that is greater than the average level observed in a corresponding control biological fluid. In some cases, a biological fluid can be evaluated to determine if the fluid has a prostate cancer fluid profile.

Any type of biological sample can be evaluated to determine if it contains one or more than one nucleic acid or polypeptide, or fragment thereof, encoded by a nucleic acid listed in Table 4 at a level that is greater than the average level observed in a corresponding control biological sample. For example, biological fluids can be evaluated including, without limitation, blood, plasma, serum, urine, semen, and seminal fluid. In some cases, prostate cells can be evaluated including, without limitation, prostate cells in prostate tissue and metastatic prostate cancer cells in blood, urine, cellular fragments, or in tissues other than prostate tissue such as lung tissue and lymph node tissue. In some cases, prostate cells can be evaluated to determine whether or not the cells have a prostate cancer cell profile.

Any method can be used to obtain a biological sample from a mammal. For example, a blood sample can be obtained by peripheral venipuncture, and urine samples can be obtained using standard urine collection techniques. In some cases, a tissue sample can be obtained from a tissue biopsy (e.g., a needle biopsy), from a transurethral resection of the prostate (TURP), or from a radical prostatectomy. A sample can be manipulated prior to being evaluated for the level of one or more than one nucleic acid or polypeptide encoded by a nucleic acid listed in Table 2 or 3. A sample also can be manipulated prior to being evaluated for a prostate cancer fluid profile or a prostate cancer cell profile. For example, a prostate biopsy specimen can be frozen, embedded, and/or sectioned prior to being evaluated. In addition, nucleic acids and/or polypeptides can be extracted from a sample, purified, and evaluated to determine the level of one or more than one nucleic acid or polypeptide encoded by a nucleic acid listed in Table 2 or 3. In some cases, nucleic acids and/or polypeptides extracted from a sample can be evaluated for a prostate cancer cell profile or a prostate cancer fluid profile. In some cases, a tissue sample can be disrupted to obtain a cell lysate. Once obtained, the cell lysate can be analyzed for the level of one or more than one polypeptide encoded by a nucleic acid listed in Table 4. A cell lysate also can be evaluated for a prostate cancer cell profile. In some cases, prostate cells can be isolated from other cells or tissues prior to analysis. For example, prostate cells can be isolated from tissues using laser capture microdissection prior to being evaluated for the level of one or more than one nucleic acid or polypeptide encoded by a nucleic acid listed in Table 4. In some cases, prostate cells can be evaluated for a prostate cancer cell profile.

The level of any number of nucleic acids or polypeptides encoded by nucleic acids listed in Table 2 can be evaluated to identify prostate cancer. For example, the level of one or more than one (e.g., two, three, four, five, six, seven, eight, nine, 10, 15, 20, 25, 30, 35, 40, 45, 50, 55, 60, or more than 60) nucleic acid or polypeptide encoded by a nucleic acid listed in Table 2 can be used to identify prostate cancer. In some cases, the level of one or more than one (e.g., two, three, four, five, six, seven, eight, nine, 10, 15, 20, 25, 30, 35, 40, 45, 50, 55, 60, or more than 60) nucleic acid or polypeptide encoded by a nucleic acid listed in Table 2, and the level of one or more than one (e.g., two, three, four, five, six, or more than 6) nucleic acid or polypeptide encoded by a nucleic acid listed in Table 3 can be used to identify prostate cancer. In some cases, the level of one or more than one (e.g., two, three, four, five, six, seven, eight, nine, 10, 15, 20, 25, 30, 35, 40, 45, 50, or more than 50) nucleic acid or polypeptide encoded by a nucleic acid listed in Table 4 can be used to identify prostate cancer.

The level of a nucleic acid or polypeptide encoded by a nucleic acid listed in Table 2 or 3 in a biological sample can be greater than or less than the average level observed in corresponding control samples. Typically, a nucleic acid or polypeptide can be classified as being present at a level that is greater than or less than the average level observed in control samples if the levels differ by at least 10, 20, 30, 40, 50, 60, 70, 80, 90, or more percent. In some cases, a nucleic acid or polypeptide can be classified as being present at a level that is greater than or less than the average level observed in control samples if the levels differ by greater than 1-fold (e.g., 1.5-fold, 2-fold, 3-fold, or more than 3-fold). Control samples typically are obtained from one or more mammals of the same species as the mammal being evaluated. When identifying prostate cancer, control samples (e.g., control serum or urine samples) can be obtained from healthy mammals, such as male humans who do not have prostate cancer. In some cases, control samples can be non-cancerous prostate cells or tissues from male mammals having prostate cancer (e.g., non-neoplastic cells adjacent to prostate cancer cells). Control samples can be obtained from any number of mammals. For example, control samples can be obtained from one or more mammals (e.g., 10, 20, 30, 40, 50, 75, 100, 200, 300, 400, 500, 1000, or more than 1000 mammals) from the same species as the mammal being evaluated.

Any method can be used to determine whether or not a polypeptide is present in a biological sample at a level that is greater than or less than the average level observed in corresponding control samples. For example, the level of a particular polypeptide can be measured using, without limitation, immuno-based assays (e.g., ELISA and immunohistochemistry), Western blotting, arrays for detecting polypeptides, two-dimensional gel analysis, chromatographic separation, mass spectrometry (MS), tandem mass spectrometry (MS/MS), or liquid chromatography (LC)-MS. Methods of using arrays for detecting polypeptides include, without limitation, those described herein. Such methods can be used to determine simultaneously the relative levels of multiple polypeptides.

Any method can be used to determine whether or not a specific nucleic acid is present in a biological samples at a level that is greater than or less than the average level observed in corresponding control samples. For example, the level of a particular nucleic acid can be measured using, without limitation, Northern blotting, slot blotting, quantitative PCR, RT-PCR, or chip hybridization techniques. Methods for chip hybridization assays include, without limitation, those described herein. Such methods can be used to determine simultaneously the relative expression levels of multiple nucleic acids.

Methods provided herein for identifying prostate cancer in male mammals can be used in combination with one or more methods typically used to identify prostate cancer. Such methods include, without limitation, digital rectal exam, transrectal ultrasonography, intravenous pyelogram, cystoscopy, and blood and urine tests for levels of prostatic acid phosphatase (PAP) and PSA. A mammal can be evaluated regularly for prostate cancer. For example, a mammal can be evaluated once a year for as long as the mammal is alive. In some cases, male humans can be evaluated for prostate cancer once every year beginning at age 35. Mammals that are susceptible to develop prostate cancer can be screened more frequently, and screening can be started at an earlier age. For example, mammals having a genetic predisposition to develop cancer, a family history of cancer, or a trend towards an increased serum level of one or more polypeptides encoded by a nucleic acid listed in Table 2 can be assessed more frequently.

This document also provides materials and methods for assessing prostate cancer in a mammal. For example, this document provides materials and methods for assessing the aggressiveness of prostate cancer in a mammal. Methods typically used to assess the aggressiveness of prostate cancer in a mammal include determining the Gleason score, the serum PSA level, and whether or not the serum PSA level increases over time and rate of PSA increases (PSA velocity). The Gleason score is a measure of how different cancer cells are from normal cells. The more different the cancer cells are from non-cancer cells, the more likely that the cancer will spread quickly. In some cases, the aggressiveness of prostate cancer can be assessed based on the numbers and/or levels of nucleic acids or polypeptides encoded by nucleic acids listed in Table 2 in a biological fluid from a mammal. The greater the number of different nucleic acids or polypeptides encoded by nucleic acids listed in Table 2 in a biological fluid from the mammal, the more aggressive the prostate cancer in the mammal. In addition, the greater the differences between the levels of the nucleic acids or polypeptides encoded by nucleic acids listed in Table 2 in a biological fluid from a mammal and the average levels of the same nucleic acids or polypeptides in control samples, the more likely the prostate cancer will move rapidly and progress in the mammal. In some embodiments, the aggressiveness of prostate cancer can be assessed based on the levels of nucleic acids or polypeptides encoded by nucleic acids listed in Table 2, and the level of one or more than one nucleic acid or polypeptide encoded by a nucleic acid listed in Table 3 in a biological fluid from a mammal. In some cases, the levels of nucleic acids or polypeptides encoded by nucleic acids listed in Table 2 in a biological fluid can be used in combination with one or more other factors to determine whether or not a mammal having prostate cancer is susceptible to a poor outcome. For example, levels of nucleic acids or polypeptides encoded by nucleic acids listed in Table 2 in a biological fluid from a mammal having prostate cancer can be used in combination with the clinical stage, the serum PSA level, and/or the Gleason pattern of the prostate cancer to determine whether or not the mammal is likely to have to a poor outcome. In some cases, the aggressiveness of prostate cancer can be assessed based on the numbers and/or levels of nucleic acids or polypeptides encoded by nucleic acids listed in Table 4 in a biological sample from a mammal.

Information about the aggressiveness of prostate cancer can be used to guide treatment selection. For example, a mammal identified as having more aggressive prostate cancer can be treated earlier and more aggressively than a mammal identified as having less aggressive prostate cancer. A more aggressive treatment can include radical prostatectomy. A mammal identified as having less aggressive prostate cancer may undergo "watchful waiting" while having little or no standard treatment, particularly if the mammal is elderly.

Once prostate cancer has been identified in a mammal (e.g., a human), the mammal can be subsequently evaluated or monitored over time for progression of the cancer, particularly if the cancer was identified as being aggressive. For example, prostate cancer in a mammal can be assessed as having progressed if it is determined that a biological fluid from the mammal (e.g., serum or urine from the mammal) contains one or more than one nucleic acid or polypeptide encoded by a nucleic acid listed in Table 2 at a level that is greater than the level of the same one or more than one nucleic acid or polypeptide observed in a corresponding biological fluid (e.g., serum or urine) obtained previously from the same mammal. In some cases, prostate cancer in a mammal can be assessed as having progressed if it is determined that a biological fluid from the mammal (e.g., serum or urine from the mammal) contains one or more than one nucleic acid or polypeptide encoded by a nucleic acid listed in Table 2, and one or more than one nucleic acid or polypeptide encoded by a nucleic acid listed in Table 3 at a level that is greater than the level of the same one or more nucleic acids or polypeptides observed in a corresponding biological fluid (e.g., serum or urine) obtained previously from the same mammal. In some cases, prostate cancer in a mammal can be assessed as having progressed if it is determined that a biological fluid from the mammal has a prostate cancer fluid profile to a level greater than that observed in a corresponding biological fluid obtained previously from the same mammal. In some cases, prostate cancer in a mammal can be assessed as having progressed if it is determined that a sample (e.g., a sample of prostate cells) from the mammal contains one or more than one nucleic acid or polypeptide encoded by a nucleic acid listed in Table 4 at a level that is greater than the level of the same one or more than nucleic acid or polypeptide observed in a corresponding sample obtained previously from the same mammal. In some cases, prostate cancer in a mammal can be assessed as having progressed if it is determined that a sample (e.g., a sample of prostate cells) from the mammal has a prostate cancer cell profile to a level greater than that observed in a corresponding sample obtained previously from the same mammal. A mammal can be monitored for progression of prostate cancer over any period of time with any frequency. For example, a male mammal can be monitored once a year, twice a year, three times a year, or more frequently. In some cases, a mammal can be monitored every three months for five years or once a year for as long as the mammal is alive.

A mammal can also be assessed for progression of prostate cancer before, during, and after treatment for prostate cancer. For example, a mammal can be assessed for progression (e.g., metastasis) of prostate cancer while being treated with androgen deprivation therapy or following radical prostatectomy. Assessing a mammal for progression of prostate cancer during treatment of the mammal for prostate cancer can allow the effectiveness of the prostate cancer therapy to be determined. For example, a decrease in the level of one or more than one nucleic acid or polypeptide encoded by a nucleic acid listed in Table 2 in a biological fluid (e.g., serum or urine) from a mammal being treated for prostate cancer as compared to the level of the same one or more nucleic acids or polypeptides observed in a corresponding biological fluid (e.g., serum or urine) obtained previously from the same mammal can indicate that the therapy is effective. In some cases, a therapy can be assessed as being effective if it is determined that a fluid from a mammal having prostate cancer and having received a prostate cancer treatment has a prostate cancer fluid profile to a level less than that observed in corresponding fluid from the same mammal prior to the treatment.

This document also provides methods and materials to assist medical or research professionals in determining whether or not a mammal has prostate cancer. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining the level of one or more than one polypeptide or nucleic acid encoded by a nucleic acid listed in Table 2 in a sample, and (2) communicating information about that level to that professional.

Any method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides arrays for detecting polypeptides. The arrays provided herein can be two-dimensional arrays, and can contain at least two different polypeptides capable of detecting polypeptides, such as antibodies (e.g., at least three, at least five, at least ten, at least 20, at least 30, at least 40, at least 50, or at least 60 different polypeptides capable of detecting polypeptides). The arrays provided herein also can contain multiple copies of each of many different polypeptides. In addition, the arrays for detecting polypeptides provided herein can contain polypeptides attached to any suitable surface (e.g., plastic or glass).

A polypeptide capable of detecting a polypeptide can be naturally occurring, recombinant, or synthetic. The polypeptides immobilized on an array also can be antibodies. An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type, (e.g., IgG, IgM, IgD, IgA or IgY), class (e.g., IgG1, IgG4, or IgA2), or subclass. In addition, an antibody can be from any animal including birds and mammals. For example, an antibody can be a mouse, chicken, human, rabbit, sheep, or goat antibody. Such an antibody can be capable of binding specifically to a polypeptide encoded by a nucleic acid listed in Table 2 or 3. The polypeptides immobilized on the array can be members of a family such as a receptor family, protease family, or an enzyme family.

Antibodies can be generated and purified using any suitable methods known in the art. For example, monoclonal antibodies can be prepared using hybridoma, recombinant, or phage display technology, or a combination of such techniques. In some cases, antibody fragments can be produced synthetically or recombinantly from a nucleic acid encoding the partial antibody sequence. In some cases, an antibody fragment can be enzymatically or chemically produced by fragmentation of an intact antibody. In addition, numerous antibodies are available commercially (Table 1). An antibody directed against a polypeptide encoded by a nucleic acid listed in Table 2 or 3 can bind the polypeptide at an affinity of at least $10^4$ mol$^{-1}$ (e.g., at least $10^5$, $10^6$, $10^7$, $10^8$, $10^9$, $10^{10}$, $10^{11}$, or $10^{12}$ mol$^{-1}$).

TABLE 1

Commercially available antibodies directed against extracellular or membrane-associated polypeptides

| Nucleic Acid Symbol | Antibody Name | Supplier | Catalog No. | Clone |
|---|---|---|---|---|
| APOC1 | Apolipoprotein C-1 antibody | Abcam, Cambridge, MA | ab20120 | mouse |
| ASPN | Asporin antibody | Imgenex, San Diego, CA | IMG-3803 | goat |
| C20orf102 | C20orf102 antibody | Abnova, Taipei, Taiwan | H00128434-M01 | clone 3B9 |
| COL2A1 | COL2A1 monoclonal antibody | Abnova, Taipei, Taiwan | H00001280-M01 | #3H1-9 |
| HLA-DMB | HLA-DMB monoclonal antibody | Abnova, Taipei, Taiwan | H00003109-M01 | clone 6B3 |
| MMP26 | Rabbit antibody to MMP-26 | Triple Point Biologics, Forest Grove, OR | RP3MMP26 | rabbit |
| NRN1 | Anti-human Neuritin antibody | R&D Systems, Minneapolis, MN | AF283 | goat |
| SFRP4 | SFRP4 polyclonal antibody | Abnova, Taipei, Taiwan | H00006424-A01 | mouse poly |
| CHRM3 | CHRM3 polyclonal antibody | Abnova, Taipei, Taiwan | H00001131-A01 | mouse poly |
| OR51E2 | PSGR antibody | Novus, Littleton, CO | ab13383 | rabbit |
| TMPRSS2 | TMPRSS2 (h-50) antibody | Santa Cruz Biotechnology, Santa Cruz, CA | sc-33533 | rabbit |
| PLA2G7 | PLA2G7 monoclonal antibody | Abnova, Taipei, Taiwan | H00007941-M02 | clone 5D1 |
| FZD8 | FZD8 polyclonal antibody | Abnova, Taipei, Taiwan | H00008325-A01 | mouse poly |
| GJB1 | Connexin 32/GJB1 antibody [CXN-32] | Abcam, Cambridge, MA | ab11366 | CXN-32 |
| MSMB | Prostate Secretory Protein/PSP antibody [YPSP-1] | Abcam, Cambridge, MA | ab19070 | YPSP-1 |
| MSMB | MSMB polyclonal antibody | Abnova, Taipei, Taiwan | H00004477-A01 | mouse poly |

TABLE 1-continued

Commercially available antibodies directed against extracellular or membrane-associated polypeptides

| Nucleic Acid Symbol | Antibody Name | Supplier | Catalog No. | Clone |
|---|---|---|---|---|
| MSMB | Mab to human Prostate Secretory protein | BIODESIGN, Saco, ME | M14841M | BDI841 |
| MSMB | Mab to human Prostate Secretory protein | BIODESIGN, Saco, ME | M14248M | BDI248 |
| MSMB | MSMB polyclonal antibody | Novus, Littleton, CO | H00004477-A01 | mouse poly |
| ADAMTS8 | ADAMTS8 antibody | Abcam, Cambridge, MA | ab28597 | rabbit |
| ADAMTS8 | ADAMTS8 monoclonal antibody | Abnova, Taipei, Taiwan | H00011095-M01 | clone 5A3 |
| ADAMTS8 | Rabbit anti ADAM-TS8, amino terminal | Accurate, Westbury, NY | ACL2ADAMTS8 | rabbit |
| ADAMTS8 | Rabbit anti ADAM-TS8, carboxy terminal | Accurate, Westbury, NY | ACL1ADAMTS8 | rabbit |
| ALDH3B2 | ALDH3B2 monoclonal antibody | Abnova, Taipei, Taiwan | H00000222-M01 | clone 3E6 |
| EFNA4 | Ephrin A4 Antibody | Novus, Littleton, CO | ab7041 | goat |
| GRIN3A | NMDAR3A+3B | Abcam, Cambridge, MA | ab2639 | mouse |
| GRIN3A | NMDAR3A+3B antibody | Novus, Littleton, CO | H00002904-A01 | mouse |
| GRIN3A | NMDAR NR3A/B antibody | QED, San Diego, CA | 60100 | rabbit |
| HPN | Hepsin antibody | Abcam, Cambridge, MA | ab31149 | Duck/IgY |
| HPN | Hepsin antibody | Abcam, Cambridge, MA | ab31148 | rabbit |
| HPN | HPN monoclonal antibody | Abnova, Taipei, Taiwan | H00003249-M01 | clone 3E3 |
| ITGBL1 | Osteoblast Specific Cysteine-rich Protein | Abcam, Cambridge, MA | ab37176 | chicken/IgY |
| LOX | LOX antibody | Abcam, Cambridge, MA | ab31238 | rabbit |
| MUC1 | MUC-1 polyclonal antibody | Abnova, Taipei, Taiwan | H00004582-A01 | mouse poly |
| NRP1 | NRP1 monoclonal antibody | Abnova, Taipei, Taiwan | H00008829-M05 | 1B3 |
| NRP1 | Anti-Neuropilin-1 (CUB Domain) | ECM Biosciences | NP2111 | rabbit |
| NRP1 | Neuropilin (A-12) antibody | Santa Cruz Biotechnology, Santa Cruz, CA | sc-5307 | mouse mono |
| PCDHB10 | PCDHB10 polyclonal antibody | Abnova, Taipei, Taiwan | H00056126-A01 | mouse poly |
| PCSK6 | PCSK6 plyclonal antibody | Abnova, Taipei, Taiwan | H00005046-A01 | mouse poly |
| PSCA | PSCA monoclonal antibody | Abnova, Taipei, Taiwan | H00008000-M03 | 5c2 |

Any method can be used to make an array for detecting polypeptides. For example, methods disclosed in U.S. Pat. No. 6,630,358 can be used to make arrays for detecting polypeptides. Arrays for detecting polypeptides can also be obtained commercially, such as from Panomics, Redwood City, Calif.

This document also provides nucleic acid arrays. The arrays provided herein can be two-dimensional arrays, and can contain at least two different nucleic acid molecules (e.g., at least three, at least five, at least ten, at least 20, at least 30, at least 40, at least 50, or at least 60 different nucleic acid molecules). Each nucleic acid molecule can have any length. For example, each nucleic acid molecule can be between 10 and 250 nucleotides (e.g., between 12 and 200, 14 and 175, 15 and 150, 16 and 125, 18 and 100, 20 and 75, or and 50 nucleotides) in length. In some cases, an array can contain one or more cDNA molecules encoding, for example, partial or entire polypeptides. In addition, each nucleic acid molecule can have any sequence. For example, the nucleic acid molecules of the arrays provided herein can contain sequences that are present within the nucleic acids listed in Tables 2 and 3.

Typically, at least 25% (e.g., at least 30%, at least 40%, at least 50%, at least 60%, at least 75%, at least 80%, at least 90%, at least 95%, or 100%) of the nucleic acid molecules of an array provided herein contain a sequence that is (1) at least 10 nucleotides (e.g., at least 11, 12, 13, 14, 15, 16, 17, 18, 19, 20, 25, or more nucleotides) in length and (2) at least about 95 percent (e.g., at least about 96, 97, 98, 99, or 100) percent identical, over that length, to a sequence present within a nucleic acid listed in Table 2 or 3. For example, an array can contain 60 nucleic acid molecules located in known positions, where each of the 60 nucleic acid molecules is 100 nucleotides in length while containing a sequence that is (1) 30 nucleotides is length, and (2) 100 percent identical, over that 30 nucleotide length, to a sequence of one of the nucleic acids listed in Table 2. Thus, a nucleic acid molecule of an array provided herein can contain a sequence present within a nucleic acid listed in Table 2 or 3 where that sequence contains one or more (e.g., one, two, three, four, or more) mismatches.

The nucleic acid arrays provided herein can contain nucleic acid molecules attached to any suitable surface (e.g., plastic or glass). In addition, any method can be use to make a nucleic acid array. For example, spotting techniques and in situ synthesis techniques can be used to make nucleic acid arrays. Further, the methods disclosed in U.S. Pat. Nos. 5,744,305 and 5,143,854 can be used to make nucleic acid arrays.

In some cases, a sample from a mammal can be assessed for auto-antibodies against a polypeptide encoded by any of the nucleic acid molecules provided herein. The presence of such auto-antibodies can indicate that the mammal has prostate cancer. For example, a blood sample from a human can be assessed for the presence of auto-antibodies to a polypeptide encoded by any of the nucleic acid molecules provided herein with the presence of such an auto-antibody indicating that that human has prostate cancer.

The invention will be further described in the following examples, which do not limit the scope of the invention described in the claims.

EXAMPLES

Example 1

Identification of Nucleic Acids Encoding Extracellular and Membrane-Associated Polypeptides that can be Used to Identify Prostate Cancer Gene expression was profiled in prostate epithelial cells. Benign and malignant cells were laser capture microdissected from 100 prostate tissues and metastatic prostatic adenocarcinomas. Non-neoplastic prostate epithelial cells were collected from the tissues of 29 patients having prostate cancer. High-grade prostatic intraepithelial neoplasia (PIN) cells, metastatic prostate cancer cells, and primary Gleason pattern 3, 4, and 5 cells were collected from the remaining tissues. RNA was extracted from homogenous populations of captured cells and purified. Samples of total RNA were linearly amplified, labeled, and hybridized to U133 Plus 2.0 arrays (Affymetrix, Santa Clara, Calif.). The arrays were washed, stained, and scanned in accordance with Affymetrix protocols.

Secreted and membrane bound polypeptides associated with the Affymetrix probe sets were identified using two methods. First, RefSeq polypeptide sequence identifiers annotated to the probe set identifiers were abstracted from the Affymetrix U133 Plus 2.0 annotation file. These sequences were downloaded from NCBI and processed through a prediction pipeline, which included SignalP analysis, TargetP analysis, TMHMM analysis, and Phobius analysis. Polypeptides predicted to be secretory polypeptides by the SignalP and TargetP programs were further analyzed using the TMHMM and Phobius programs. Polypeptides that were not predicted to be secretory polypeptides by the SignalP program or the TargetP program were classified as non-secretory polypeptides. Secretory polypeptides predicted to have no transmembrane domains by the TMHMM program were classified as extracellular. Secretory polypeptides predicted to have two or more transmembrane domains were classified as membrane-associated polypeptides. Secretory polypeptides predicted to have only one transmembrane domain were analyzed using the Phobius program. Phobius predictions were used to differentiate polypeptides with N-terminal signal anchors (uncleaved) from polypeptides with N-terminal signal sequences (cleaved). The second method used to identify secreted and membrane polypeptides involved mining the localization annotated database of SWISS-PROT polypeptides. The SwissProt records for all human polypeptides were downloaded. All localization annotations were manually reviewed and categorized as extracellular (S), plasma membrane (M), or intracellular (I). All probe sets with annotated SwissProt polypeptides having cellular localization annotations were classified extracellular (S), plasma membrane (M), or intracellular (I). Localization classifications assigned by SwissProt annotations were given preference over classifications made by the prediction analyses. A set of 70 nucleic acids encoding extracellular and membrane-associated polypeptides was identified, including 53 nucleic acids that were annotated or predicted to encode extracellular polypeptides, and 17 nucleic acids that were annotated or predicted to encode membrane-associated polypeptides.

The value of the selected nucleic acids for use in identifying cancer was assessed using two methods. Fifty-four polypeptides, including all of the membrane-associated polypeptides, were selected based on up-regulation of corresponding RNA transcripts observed in prostate cancer cells as compared to non-neoplastic prostate cells. The initial list of differentially expressed nucleic acids was identified using several microarray analysis parameters, including:

a. PM/MM normalization and no transformation
   b. PM only normalization and no transformation
   c. PM/MM normalization and log 2 transformation
   d. PM only normalization and log 2 transformation Expression values generated from these analysis methods were then used to make the following comparisons:
   a. Gleason pattern 3 versus
   Non-neoplastic (excluding Benign Prostatic Hyperplasia (BPH))
   b. Gleason pattern 3 versus
   Non-neoplastic+BPH
   c. Gleason pattern 3+Gleason pattern 4 versus
   Non-neoplastic (excluding BPH)
   d. Gleason pattern 3+Gleason pattern 4 versus
   Non-neoplastic+BPH
   e. All Cancer versus
   Non-neoplastic (excluding BPH)
   f. All Cancer versus
   Non-neoplastic+BPH Nucleic acids demonstrating at least two fold up-regulation in cancer cells compared to non-neoplastic cells were cross-referenced with nucleic acids classified as encoding either secretory or membrane-associated polypeptides. The resulting list of nucleic acids was manually curated to remove cases with expression levels below the noise level of the microarray experiment, and cases having an expression profile that was over-biased by one or two aberrant cases.

The remaining sixteen nucleic acids were selected because they had a high level of expression in prostate cells and a prostate-preferential expression profile, without clear differential expression between cancer and non-cancer cells. Tissue specificity was quantitated by mining Expressed Sequence Tag transcripts.

The 70 nucleic acids selected were cross-referenced with the Cancer Genome Anatomy Project's SAGE Genie, the Ludwig Institute for Cancer Research MPSS database, the Human Protein Atlas database, and an EST tissue specificity analysis database. Based on these additional transcriptomic and immunohistochemistry annotations, the nucleic acids were prioritized with numeric rankings from 1 (highest priority) to three (lowest priority). The selected nucleic acids are listed in Tables 2-4.

TABLE 2

Nucleic acids encoding extracellular or membrane-associated polypeptides that can be used to identify prostate cancer.

| Nucleic Acid Symbol | Selection Process | RefSeq Protein Identifier | Category | Localization |
|---|---|---|---|---|
| APOC1 | Increased expression in cancer cells versus non-cancer cells | NP_001636.1 | 1 | Extracellular |
| ASPN | Increased expression in cancer cells versus non-cancer cells | NP_060150.3 | 1 | Extracellular |
| BCMP11 | Increased expression in cancer cells versus non-cancer cells | NP_789783.1 | 1 | Extracellular |
| C20orf102 | Increased expression in cancer cells versus non-cancer cells | NP_542174.1 | 1 | Extracellular |
| COL2A1 | Increased expression in cancer cells versus non-cancer cells | NP_001835.2 NP_149162.1 | 1 | Extracellular |
| F5 | Increased expression in cancer cells versus non-cancer cells | NP_000121.1 | 1 | Extracellular |
| HLA-DMB | Increased expression in cancer cells versus non-cancer cells | NP_002109.1 | 1 | Extracellular |
| LRRN1 | Increased expression in cancer cells versus non-cancer cells | NP_065924.2 | 1 | Extracellular |
| MMP26 | Increased expression in cancer cells versus non-cancer cells | NP_068573.2 | 1 | Extracellular |
| NRN1 | Increased expression in cancer cells versus non-cancer cells | NP_057672.1 | 1 | Extracellular |
| OGDHL | Increased expression in cancer cells versus non-cancer cells | NP_060715.1 | 1 | Extracellular |
| PLA1A | Increased expression in cancer cells versus non-cancer cells | NP_056984.1 | 1 | Extracellular |
| PLA2G7 | Increased expression in cancer cells versus non-cancer cells | NP_005075.2 | 1 | Extracellular |
| SFRP4 | Increased expression in cancer cells versus non-cancer cells | NP_003005.1 | 1 | Extracellular |
| ALDH3B2 | Increased expression in cancer cells versus non-cancer cells | NP_000686.2 NP_001026786.1 | 2 | Extracellular |
| APOF | Increased expression in cancer cells versus non-cancer cells | NP_001629.1 | 2 | Extracellular |
| B3Gn-T6 | Increased expression in cancer cells versus non-cancer cells | NP_619651.2 | 2 | Extracellular |
| C4A /// C4B | Increased expression in cancer cells versus non-cancer cells | NP_001002029.1 NP_009224.2 | 2 | Extracellular |
| COL9A2 | Increased expression in cancer cells versus non-cancer cells | NP_001843.1 | 2 | Extracellular |
| COMP | Increased expression in cancer cells versus non-cancer cells | NP_000086.2 | 2 | Extracellular |
| CXCL11 | Increased expression in cancer cells versus non-cancer cells | NP_005400.1 | 2 | Extracellular |
| CXCL14 | Increased expression in cancer cells versus non-cancer cells | NP_004878.2 | 2 | Extracellular |
| CXCL9 | Increased expression in cancer cells versus non-cancer cells | NP_002407.1 | 2 | Extracellular |
| DHRS8 | Increased expression in cancer cells versus non-cancer cells | NP_057329.1 | 2 | Extracellular |

TABLE 2-continued

Nucleic acids encoding extracellular or membrane-associated polypeptides that can be used to identify prostate cancer.

| Nucleic Acid Symbol | Selection Process | RefSeq Protein Identifier | Category | Localization |
|---|---|---|---|---|
| ITGBL1 | Increased expression in cancer cells versus non-cancer cells | NP_004782.1 | 2 | Extracellular |
| LOX | Increased expression in cancer cells versus non-cancer cells | NP_002308.2 | 2 | Extracellular |
| MUC1 | Increased expression in cancer cells versus non-cancer cells | NP_001018016.1 NP_001018017.1 NP_001018021.1 NP_002447.4 | 2 | Extracellular |
| OR51E1 | Increased expression in cancer cells versus non-cancer cells | NP_689643.1 | 2 | Extracellular |
| PCSK6 | Increased expression in cancer cells versus non-cancer cells | NP_002561.1 NP_612192.1 NP_612193.1 NP_612194.1 NP_612195.1 NP_612196.1 NP_612197.1 NP_612198.2 | 2 | Extracellular |
| RPL22L1 | Increased expression in cancer cells versus non-cancer cells | XP_498952.2 XP_940025.1 XP_947405.1 XP_950994.1 | 2 | Extracellular |
| C1orf64 | Increased expression in cancer cells versus non-cancer cells | NP_849162.1 | 3 | Extracellular |
| CCL19 | Increased expression in cancer cells versus non-cancer cells | NP_006265.1 | 3 | Extracellular |
| NRP1 | Increased expression in cancer cells versus non-cancer cells | NP_001019799.1 NP_001019800.1 NP_003864.3 | 3 | Extracellular |
| SFTPA2 | Increased expression in cancer cells versus non-cancer cells | NP_008857.1 | 3 | Extracellular |
| CDH10 | Increased expression in cancer cells versus non-cancer cells | NP_006718.2 | 1 | Membrane-associated |
| CDH7 | Increased expression in cancer cells versus non-cancer cells | NP_004352.2 NP_387450.1 | 1 | Membrane-associated |
| CHRM3 | Increased expression in cancer cells versus non-cancer cells | NP_000731.1 | 1 | Membrane-associated |
| FZD8 | Increased expression in cancer cells versus non-cancer cells | NP_114072.1 | 1 | Membrane-associated |
| GJB1 | Increased expression in cancer cells versus non-cancer cells | NP_000157.1 | 1 | Membrane-associated |
| MS4A8B | Increased expression in cancer cells versus non-cancer cells | NP_113645.1 | 1 | Membrane-associated |
| OR51E2 | Increased expression in cancer cells versus non-cancer cells | NP_110401.1 | 1 | Membrane-associated |
| SLC43A1 | Increased expression in cancer cells versus non-cancer cells | NP_003618.1 | 1 | Membrane-associated |
| TMEM45B | Increased expression in cancer cells versus non-cancer cells | NP_620143.1 | 1 | Membrane-associated |
| FAM77C | Increased expression in cancer cells versus non-cancer cells | NP_078798.1 | 2 | Membrane-associated |
| GPR116 | Increased expression in cancer cells versus non-cancer cells | NP_056049.3 | 2 | Membrane-associated |
| GRIN3A | Increased expression in cancer cells versus non-cancer cells | NP_597702.1 | 2 | Membrane-associated |

TABLE 2-continued

Nucleic acids encoding extracellular or membrane-associated polypeptides that can be used to identify prostate cancer.

| Nucleic Acid Symbol | Selection Process | RefSeq Protein Identifier | Category | Localization |
|---|---|---|---|---|
| HPN | Increased expression in cancer cells versus non-cancer cells | NP_002142.1 NP_892028.1 | 2 | Membrane-associated |
| PCDHB10 | Increased expression in cancer cells versus non-cancer cells | NP_061753.1 | 2 | Membrane-associated |
| PCDHGA4 | Increased expression in cancer cells versus non-cancer cells | NP_061740.1 NP_114442.1 | 2 | Membrane-associated |
| PRG-3 | Increased expression in cancer cells versus non-cancer cells | NP_060223.2 NP_997182.1 | 2 | Membrane-associated |
| RET | Increased expression in cancer cells versus non-cancer cells | NP_065681.1 NP_066124.1 | 2 | Membrane-associated |
| ACPP | High-level, prostate-preferential expression | NP_001090.2 | 1 | Extracellular |
| FAM61B | High-level, prostate-preferential expression | NP_653304.1 | 1 | Extracellular |
| MSMB | High-level, prostate-preferential expression | NP_002434.1 NP_619540.1 | 1 | Extracellular |
| PGLS | High-level, prostate-preferential expression | NP_036220.1 | 1 | Extracellular |
| RBM35A | High-level, prostate-preferential expression | NP_001030087.1 NP_060167.2 | 1 | Extracellular |
| TMPRSS2 | High-level, prostate-preferential expression | NP_005647.2 | 1 | Extracellular |
| LOC284591 | High-level, prostate-preferential expression | XP_932207.1 XP_941863.1 | 2 | Extracellular |
| ADAMTS8 | High-level, prostate-preferential expression | NP_008968.3 | 2 | Extracellular |
| EFNA4 | High-level, prostate-preferential expression | NP_005218.1 NP_872631.1 NP_872632.1 | 3 | Extracellular |
| KAZALD1 | High-level, prostate-preferential expression | NP_112191.2 | 3 | Extracellular |
| SEMA3F | High-level, prostate-preferential expression | NP_004177.2 | 3 | Extracellular |
| UCN | High-level, prostate-preferential expression | NP_003344.1 | 3 | Extracellular |
| PRAC2 | High-level, prostate-preferential expression | Entrez Gene 360205 | 3 | Extracellular |

TABLE 3

Nucleic acids encoding extracellular polypeptides that can be used in combination with one or more polypeptides encoded by nucleic acids listed in Table 2 to identify prostate cancer.

| Nucleic Acid Symbol | Selection Process | RefSeq Protein Identifier | Category | Localization |
|---|---|---|---|---|
| CRISP3 | Increased expression in cancer cells versus non-cancer cells | NP_006052.1 | 1 | Extracellular |
| AMACR | Increased expression in cancer cells versus non-cancer cells | NP_055139.4 NP_976316.1 | 3 | Extracellular |
| KLK2 | High-level, prostate-preferential expression | NP_001002231.1 NP_001002232.1 NP_005542.1 | 1 | Extracellular |
| KLK3 | High-level, prostate-preferential expression | NP_001025218.1 NP_001025219.1 NP_001025220.1 NP_001025221.1 NP_001639.1 | 1 | Extracellular |
| KLK4 | High-level, prostate-preferential expression | NP_004908.2 | 2 | Extracellular |
| PSCA | High-level, prostate-preferential expression | NP_005663.1 | 2 | Extracellular |

TABLE 4

Nucleic acids encoding extracellular or membrane-associated polypeptides that are differentially expressed in cancerous and non-cancerous prostate epithelial cells.

| Nucleic Acid Symbol | Selection Process | RefSeq Protein Identifier | Category | Localization |
|---|---|---|---|---|
| APOC1 | Increased expression in cancer cells versus non-cancer cells | NP_001636.1 | 1 | Extracellular |
| ASPN | Increased expression in cancer cells versus non-cancer cells | NP_060150.3 | 1 | Extracellular |
| BCMP11 | Increased expression in cancer cells versus non-cancer cells | NP_789783.1 | 1 | Extracellular |
| C20orf102 | Increased expression in cancer cells versus non-cancer cells | NP_542174.1 | 1 | Extracellular |
| COL2A1 | Increased expression in cancer cells versus non-cancer cells | NP_001835.2 NP_149162.1 | 1 | Extracellular |
| F5 | Increased expression in cancer cells versus non-cancer cells | NP_000121.1 | 1 | Extracellular |
| HLA-DMB | Increased expression in cancer cells versus non-cancer cells | NP_002109.1 | 1 | Extracellular |
| LRRN1 | Increased expression in cancer cells versus non-cancer cells | NP_065924.2 | 1 | Extracellular |
| MMP26 | Increased expression in cancer cells versus non-cancer cells | NP_068573.2 | 1 | Extracellular |
| NRN1 | Increased expression in cancer cells versus non-cancer cells | NP_057672.1 | 1 | Extracellular |
| OGDHL | Increased expression in cancer cells versus non-cancer cells | NP_060715.1 | 1 | Extracellular |
| PLA1A | Increased expression in cancer cells versus non-cancer cells | NP_056984.1 | 1 | Extracellular |
| PLA2G7 | Increased expression in cancer cells versus non-cancer cells | NP_005075.2 | 1 | Extracellular |
| SFRP4 | Increased expression in cancer cells versus non-cancer cells | NP_003005.1 | 1 | Extracellular |
| ALDH3B2 | Increased expression in cancer cells versus non-cancer cells | NP_000686.2 NP_001026786.1 | 2 | Extracellular |
| APOF | Increased expression in cancer cells versus non-cancer cells | NP_001629.1 | 2 | Extracellular |
| B3Gn-T6 | Increased expression in cancer cells versus non-cancer cells | NP_619651.2 | 2 | Extracellular |
| C4A /// C4B | Increased expression in cancer cells versus non-cancer cells | NP_001002029.1 NP_009224.2 | 2 | Extracellular |
| COL9A2 | Increased expression in cancer cells versus non-cancer cells | NP_001843.1 | 2 | Extracellular |
| COMP | Increased expression in cancer cells versus non-cancer cells | NP_000086.2 | 2 | Extracellular |
| CXCL11 | Increased expression in cancer cells versus non-cancer cells | NP_005400.1 | 2 | Extracellular |
| CXCL14 | Increased expression in cancer cells versus non-cancer cells | NP_004878.2 | 2 | Extracellular |
| CXCL9 | Increased expression in cancer cells versus non-cancer cells | NP_002407.1 | 2 | Extracellular |
| DHRS8 | Increased expression in cancer cells versus non-cancer cells | NP_057329.1 | 2 | Extracellular |

TABLE 4-continued

Nucleic acids encoding extracellular or membrane-associated polypeptides that are differentially expressed in cancerous and non-cancerous prostate epithelial cells.

| Nucleic Acid Symbol | Selection Process | RefSeq Protein Identifier | Category | Localization |
|---|---|---|---|---|
| ITGBL1 | Increased expression in cancer cells versus non-cancer cells | NP_004782.1 | 2 | Extracellular |
| LOX | Increased expression in cancer cells versus non-cancer cells | NP_002308.2 | 2 | Extracellular |
| MUC1 | Increased expression in cancer cells versus non-cancer cells | NP_001018016.1 NP_001018017.1 NP_001018021.1 NP_002447.4 | 2 | Extracellular |
| OR51E1 | Increased expression in cancer cells versus non-cancer cells | NP_689643.1 | 2 | Extracellular |
| PCSK6 | Increased expression in cancer cells versus non-cancer cells | NP_002561.1 NP_612192.1 NP_612193.1 NP_612194.1 NP_612195.1 NP_612196.1 NP_612197.1 NP_612198.2 | 2 | Extracellular |
| RPL22L1 | Increased expression in cancer cells versus non-cancer cells | XP_498952.2 XP_940025.1 XP_947405.1 XP_950994.1 | 2 | Extracellular |
| C1orf64 | Increased expression in cancer cells versus non-cancer cells | NP_849162.1 | 3 | Extracellular |
| CCL19 | Increased expression in cancer cells versus non-cancer cells | NP_006265.1 | 3 | Extracellular |
| NRP1 | Increased expression in cancer cells versus non-cancer cells | NP_001019799.1 NP_001019800.1 NP_003864.3 | 3 | Extracellular |
| SFTPA2 | Increased expression in cancer cells versus non-cancer cells | NP_008857.1 | 3 | Extracellular |
| CDH10 | Increased expression in cancer cells versus non-cancer cells | NP_006718.2 | 1 | Membrane-associated |
| CDH7 | Increased expression in cancer cells versus non-cancer cells | NP_004352.2 NP_387450.1 | 1 | Membrane-associated |
| CHRM3 | Increased expression in cancer cells versus non-cancer cells | NP_000731.1 | 1 | Membrane-associated |
| FZD8 | Increased expression in cancer cells versus non-cancer cells | NP_114072.1 | 1 | Membrane-associated |
| GJB1 | Increased expression in cancer cells versus non-cancer cells | NP_000157.1 | 1 | Membrane-associated |
| MS4A8B | Increased expression in cancer cells versus non-cancer cells | NP_113645.1 | 1 | Membrane-associated |
| OR51E2 | Increased expression in cancer cells versus non-cancer cells | NP_110401.1 | 1 | Membrane-associated |
| SLC43A1 | Increased expression in cancer cells versus non-cancer cells | NP_003618.1 | 1 | Membrane-associated |
| TMEM45B | Increased expression in cancer cells versus non-cancer cells | NP_620143.1 | 1 | Membrane-associated |
| FAM77C | Increased expression in cancer cells versus non-cancer cells | NP_078798.1 | 2 | Membrane-associated |
| GPR116 | Increased expression in cancer cells versus non-cancer cells | NP_056049.3 | 2 | Membrane-associated |
| GRIN3A | Increased expression in cancer cells versus non-cancer cells | NP_597702.1 | 2 | Membrane-associated |

TABLE 4-continued

Nucleic acids encoding extracellular or membrane-associated polypeptides that are differentially expressed in cancerous and non-cancerous prostate epithelial cells.

| Nucleic Acid Symbol | Selection Process | RefSeq Protein Identifier | Category | Localization |
|---|---|---|---|---|
| HPN | Increased expression in cancer cells versus non-cancer cells | NP_002142.1 NP_892028.1 | 2 | Membrane-associated |
| PCDHB10 | Increased expression in cancer cells versus non-cancer cells | NP_061753.1 | 2 | Membrane-associated |
| PCDHGA4 | Increased expression in cancer cells versus non-cancer cells | NP_061740.1 NP_114442.1 | 2 | Membrane-associated |
| PRG-3 | Increased expression in cancer cells versus non-cancer cells | NP_060223.2 NP_997182.1 | 2 | Membrane-associated |
| RET | Increased expression in cancer cells versus non-cancer cells | NP_065681.1 NP_066124.1 | 2 | Membrane-associated |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An enzyme-linked immunosorbent assay method for identifying a male human as having prostate cancer, said method comprising:
    (a) obtaining a serum sample of a male human,
    (b) performing an enzyme-linked immunosorbent assay to detect the presence of an elevated level of a polypeptide encoded by an ASPN, PCSK6, RPL22L1, or CDH7 nucleic acid within said sample, and
    (c) classifying said male human as having prostate cancer based at least in part on said presence.

2. The method of claim 1, wherein said polypeptide is a polypeptide encoded by said ASPN nucleic acid.

3. The method of claim 1, wherein said polypeptide is a polypeptide encoded by said PCSK6 nucleic acid.

4. The method of claim 1, wherein said polypeptide is a polypeptide encoded by said RPL22L1 nucleic acid.

5. The method of claim 1, wherein said polypeptide is a polypeptide encoded by said CDH7 nucleic acid.

* * * * *